US007267946B2

(12) United States Patent
Runge et al.

(10) Patent No.: US 7,267,946 B2
(45) Date of Patent: Sep. 11, 2007

(54) MITOCHONDRIAL DNA DAMAGE AS A PREDICTOR OF CORONARY ATHEROSCLEROTIC HEART DISEASE

(75) Inventors: Marschall S. Runge, Chapel Hill, NC (US); Bennett VanHouten, Durham, NC (US); Scott W. Ballinger, Santa Fe, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/832,069

(22) Filed: Apr. 10, 2001

(65) Prior Publication Data

US 2003/0040495 A1    Feb. 27, 2003

Related U.S. Application Data

(63) Continuation-in-part of application No. 09/231,093, filed on Jan. 14, 1999, now Pat. No. 6,322,974.

(51) Int. Cl.
*C07H 21/04* (2006.01)
*C12Q 1/68* (2006.01)

(52) U.S. Cl. .................. 435/6; 435/91.1; 435/91.2; 536/24.3; 536/23.5

(58) Field of Classification Search .................. 435/6, 435/91.1, 91.2; 536/24.3, 23.5
See application file for complete search history.

(56) References Cited

U.S. PATENT DOCUMENTS 5,989,816 A * 11/1999 Van Houten .................... 435/6
6,218,117 B1 * 4/2001 Herrnstadt et al. ............ 435/6
6,322,974 B1 * 11/2001 Runge et al. .................. 435/6

OTHER PUBLICATIONS

Yan et al. "In vivo evidence of the releationship of reactive oxygen species and mitochondrial DNA damage in atheroclerosis". Circulation. vol. 96, No. 8, abstract 3373, Oct. 1997.*
Corral-Debrinski et al. "Association of mitochondrial DNA damage with aging and coronary atherosclerotic heart disease". Mutation Research, vol. 275, p. 169-180, 1992.*
Ferrari, Roberto, "The role of mitochondria in ischemic heart disease". J. of Cardiovascular Pharmacology, vol. 28, Suppl. 1, p. S1-S10, 1996.*
Corral-Debrinski et al. "Hypoxemia is associated with mtDNA damage and gene induction." pagesd 1812-1816, vol. 266, No. 13, Oct. 1991.*
Berlett et al. "Protein oxidation in aging, disease and oxidative stress." J of Biol. Chem. vol. 272, No. 33, pp. 20313-20316 Aug. 1997.*
VenMurthy et al. (Acta Biochimica Polonica, vol. 43, No. 1, pp. 227-240, 1996).*
Filser et al. (Biochemical and Biophysical Research Comm. vol. 233, pp. 102-107, 1997).*

Adachi et al., "A deletion of mitochondrial DNA in murine doxorubicin-induced cardiotoxicity," *Biochem Biophys Res Commun*, 195(2):945-951, 1993.
Andreassi, "Coronary atherosclerosis and somatic mutations: an overview of the contributive factors for oxidative DNA damage," *Mutation Research*, 543:67-86, 2003.
Attardi et al., "New insights into the mechanisms of RNA synthesis and processing in human mitochondria," In: *Achievements and Perspectives of Mitochondrial Research*, eds Qkuagliarello et al., Elsevier Science, NY, 145-163, 1985.
Ballinger et al., "Hydrogen peroxide- and peroxynitrite-induced mitochondrial DNA damage and dysfunction in vascular endothelial and smooth muscle cells," *Circulation Research*, 86:960-966. 2000.
Ballinger et al., "Mitochondrial genome damage associated with cigarette smoking," *Cancer Res.*, 56(24):5692-5697, 1996.
Ballinger et al., "Maternally transmitted diabetes and deafness associated with a 10.4 kb mitochondrial DNA deletion," *Nature Genet*, 1(1):11-15, 1992.
Ballinger et al., "Mitochondrial integrity and function in atherogenesis," *Circulation*, 106:554-549, 2002.
Bandy et al., "Mitochondrial mutations may increase oxidative stress: implications for carcinogenesis and aging?" *Free Rad Biol Med*, 8(6):523-539, 1990.
Bason et al., "Interaction of antibodies against cytomegalovirus with heat-shock protein 60 in pathogenesis of atherosclerosis," The Lancet, 362:1971-1977, 2003.
Berg et al., "A new sensitive bioassay for precise quantification of interferon activity as measured via the mitochondrial dehydrogenase function in cells (MTT-method)," *APMIS*, 98:152-162, 1990.
Bindoli, "Lipid peroxidation in mitochondria," *Free Rad Biol Med*, 5(4):247-261, 1988.
Blanc et al., "Protective role of uncoupling protein 2 in atherosclerosis," *Circulation*, 107:388-390, 2003.
Chen et al., "Senescence-like growth arrest induced by hydrogen peroxide in human diploid fibroblast F65 cells," *Proc. Natl. Acad. Sci., USA*, 91:4130-4134, 1994.
Christianson et al., "A tridecamer DNA sequence supports human mitochondrial RNA 3'-end formation in vitro," *Mol. Cell Biol.*, 8(10):4502-4509, 1988.
Christianson et al., "In vitro transcription of human mitochondrial DNA: accurate termination requires a region of DNA sequence that can function bidirectionally," *Proc. Natl. Acad. Sci., USA*, 83(17):6277-6281, 1986.
Cortopassi et al., "Detection of a specific mitochondrial DNA deletion in tissues of older humans," *Nucleic Acids Research*, 18(23):6927-2933, 1990.

(Continued)

*Primary Examiner*—Jeanine A Goldberg
(74) *Attorney, Agent, or Firm*—Fulbright & Jaworski L.L.P.

(57) ABSTRACT

The present invention demonstrates that mitochondrial DNA damage occurs prior to, or simultaneous with, atherosclerotic lesion development, that aortic mitochondrial DNA damage increases with age, and that genotype and diet both influence the level of mitochondrial DNA damage. Hence, the present invention demonstrates that mitochondrial DNA damage occurs early in atherosclerosis, and may be an initiating event in atherogenesis, and provides methods to predict coronary atherosclerotic heart disease based upon the amount of mitochondrial DNA damage.

13 Claims, 20 Drawing Sheets

OTHER PUBLICATIONS

Darley-Usmar et al., "The simultaneous generation of superoxide and nitric oxide can initiate lipid peroxidation in human low density lipoprotein," *Free Radical Res Commun*, 17:9-20, 1992.

Diaz et al., "Antioxidants and atherosclerotic heart disease," *New England Journal of Medicine*, 337(6):408-416, 1997.

Doerson et al., "Characterization of an Rnase P activity from HeLa cell mitochondria. Comparison with the cytosol Rnase P activity," *J. Biol. Chem.*, 260(10):5942-5949, 1985.

Ferrari et al., "Oxygen-mediated myocardial damage during ischaemia and reperfusion: role of the cellular defences against oxygen toxicity," *J Mol Cell Cardiol*, 17:937-945, 1985.

Finkel and Holbrook, "Oxidants, oxidative stress and the biology of ageing," *Nature*, 408:239-2447, 2000.

Fossel et al., "Cell death induced by peroxidized low-density lipoprotein: endopepsis," *Cancer Res.*, 54(5):1240-1248, 1994.

Giulivi et al., "Hydroxyl radical generation during mitochondrial electron transfer and the formation of 8-hydroxydesoxyguanosine in mitochondrial DNA," *Arch Biochem Biophys*, 316(2):909-916, 1995.

Goda et al., "Modulation of mitochondrion-mediated oxidative stress by nitric oxide in human placental trophoblastic cells," *Am J Physiol*, 271:H1893-1899, 1996.

Graham et al., "Peroxynitrate modification of low-density lipoprotein leads to recognition by the macrophage scavenger receptor," *FEBS Lett*, 330:181-185, 1993.

Heitzer et al., "Endothelial dysfunction, oxidative stress, and risk of cardiovascular events in patients with coronary artery disease," *Circulation*, 104:2673-2678, 2001.

Holland et al., "Atherogenic levels of low-density lipoprotein increase hydrogen peroxide generation in cultured human endothelial cells: possible mechanism of heightened endocytosis," *J. Cell Phys*, 166(1):144-151, 1996.

Hruszkewyca, "Lipid peroxidation and mtDNA degeneration. A hypothesis," *Mut. Res*, 275(3-6):243-248, 1992.

Huet et al., "NADH-dependent dehydrogenase activity estimation by flow cytometric analysis of 3-(4,5-dimethylthiazolyl-2-yl)-2,5-diphenyltetrazolium bromide (MTT) reduction," *Cytometry*, 13(5):532-539, 1992.

Knight-Lozano et al., "Cigarette smoke exposure and hypercholesterolemia increase mitochondrial damage in cardiovascular tissues," *Circulation*, 105:849-854, 2002.

Leibovitz et al., "Neurodegeneration, myocardial injury, and perinatal death in mitochondrial superoxide dismutase-deficient mice," *Proc. Natl. Acad. Sci., USA*, 93:9782-9787, 1996.

Lippold, "Quantification succinic deydrogenases histochemistry," *Histochemistry*, 76:381-405, 1982.

Malek et al., "Hemodynamic shear stress and its role in atherosclerosis," *JAMA*, 282:2035-2042, 1999.

McCord, "Free radicals and myocardial ischemia: overview and outlook," *Free Rad Biol Med*, 4(1):9-14, 1988.

Nomiyama et al., "Accumulation of somatic mutation in mitochondrial DNA and atherosclerosis in diabetic patients," *Ann NY Acad Sci*, 1011:193-204, 2004.

Ojala et al., "The tRNA genes punctuate the reading of genetic information in human mitochondrial DNA," *Cell*, 22(2 pt 2):393-403, 1980.

Ojala et al., "tRNA punctuation model of RNA processing in human mitochondria," *Nature*, 29(5806):470-474, 1981.

Parthasarathy et al., "Role of oxidized low density lipoprotein in atherogenesis," *Prog Lipid Res*, 31:127-143, 1992.

Sastre et al., "Aging of the liver: age-associated mitochondrial damage in intact hepatocytes," *Hepatology*, 24(5):1199-1205, 1996.

Shigenaga et al., "Oxidative damage and mitochondrial decay in aging," *Proc. Natl. Acad. Sci., USA*, 91:10771-10778, 1994.

Slater et al., "Studies on succinate-tetrazolium reductase systems," *Biochim Biophys Acta*, , 77:383-393, 1963.

Sorescu et al., Superoxide production and expression of nox family proteins in human atherosclerosis, *Circulation*, 105:r40-r46, 2002.

Steinberg et al., "Is the oxidative modification hypothesis relevant to human atherosclerosis?" *Circulation*, 105:2107-2111, 2002.

Stöllberger and Finsterer, "Atherosclerosis: infection-induced involvement of mitochondrial chaperonins," *The Lancet*, 362:1949-1950, 2003.

Topper et al., "Identification of vascular endothelial genes differentially responsive to fluid mechanical stimuli: cyclooxygenase-2, manganese superoxide dismutase, and endothelial cell nitric oxide synthase are selectively up-regulated by steady laminar shear stress," *Proc. Natl. Acad. Sci., USA*, 93:10417-10422, 1996.

Trounce et al., "Decline in skeletal muscle mitochondrial respiratory chain function: possible factor in ageing," *Lancet*, 333(8639):637-639, 1989.

Williams et al., "Increased oxidative damage is correlated to altered mitochondrial function in heterozygous manganese superoxide dismutase knockout mice," *J. Biol. Chem.*, 273(43):28510-28515, 1998.

Williams, "Canaries in the coal mine: mitochondrial DNA and vascular injury from reactive oxygen species," *Circulation Res.*, 86:915-916, 2000.

Yakes et al., "PCR-based assays for the detection and quantification of DNA damage and repair," In: *Technologies for Detection of DNA Damage and Mutations*, Pfeifer ed, Plenum, NY, 169-182, 1996.

Yakes et al., "Mitochondrial DNA damage is more extensive and persists longer than nuclear DNA damage in human cells following oxidative stress," *Proc. Natl. Acad. Sci., USA*, 94(2):514-519, 1997.

Zhang et al., "The oxidative inactivation of mitochondrial electron transport chain components and ATPase," *J. Biol. Chem.*, 265(27):16330-16336, 1990.

Cadenas and Davies, "Oxidative inactivation and proteolytic degradation of mitochondrial proteins," *Free Radical Biology and Medicine*, 29:222-230, 2000. (Abstract Only).

Halmosi et al., "Effect of poly(ADP-ribose) polymerase inhibitors on the ischemia-reperfusion-induced oxidative cell damage and mitochondrial metabolism in Langendorff heart perfusion system" *Mol. Pharmacol.*, 59(6):1497-1505, 2001.

\* cited by examiner $^{35}$S-Methionine Incorporation (% of control)

|  | Control | 0.2 mM $H_2O_2$ | 0.1 mM ONOO⁻ | 0.5 mM ONOO⁻ |
|---|---|---|---|---|
| HASMC | 100 | 67 | 88 | 30 |
| HUVEC | 100 | 77 | ND | 45 |

Fig. 4B

A. Mitochondrial DNA Damage
in Control and apoE -/- Aortas

B

| Control | apoE -/- | P value |
|---|---|---|
| 0.0 (0.15) | 1.36 (0.16) | 0.001 |

* significantly different (P < 0.05) from 4% diet

* Significantly different from non-exercised counterpart

MITOCHONDRIAL DNA DAMAGE AS A PREDICTOR OF CORONARY ATHEROSCLEROTIC HEART DISEASE

CROSS-REFERENCE TO RELATED APPLICATION

This non-provisional patent application is a continuation-in-part of U.S. Ser. No. 09/231,093, filed Jan. 14, 1999, now U.S. Pat. 6,322,974.

FEDERAL FUNDING LEGEND

This invention was created in part using funds obtained through grants HL59652 and ES 09318 from the National Institutes of Health. Consequently, the federal government has certain rights in this invention.

BACKGROUND OF THE INVENTION

1. Field of the Invention

The present invention relates generally to the field of physiology and molecular biology. More specifically, the present invention relates to DNA damage and the effects of DNA damage on atherosclerosis.

2. Description of the Related Art

Reactive oxygen species (reactive oxygen species) have been suggested to play a critical role in the pathogenesis of atherosclerotic lesions (1-6), but the underlying mechanisms have not yet been elucidated. For example, reactive oxygen species-mediated mechanisms are likely to be a significant factor in the oxidation of LDL (ox-LDL), a key event in atherogenesis (3,7,8). Studies have shown that both superoxide ($O_2^-$) and peroxynitrite (peroxynitrite; formed from $O_2^-$ + nitric oxide) are capable of oxidizing LDL (9-11). Hence, reactions involving nitric oxide and/or $O_2^-$ are believed to play a critical role in the pathogenesis of atherosclerotic lesions and impaired vascular function (i.e. endothelial cell dysfunction), with the actions of their oxidizing products ($H_2O_2$, peroxynitrite) not yet well defined.

The mitochondrion is a major source of cellular reactive oxygen species ($O_2^-$), which are formed during electron transport (12-16). These reactive oxygen species are capable of preferentially damaging the mitochondrial membranes and proteins (17-19), affecting key cell functions, including mitochondrial respiration, which, if altered, leads to increased reactive oxygen species production (20-22), mediating lipid peroxidation (23, 24) and DNA damage (25, 26). Because mitochondrial oxidative phosphorylation (OXPHOS) capacities decline as mitochondrial DNA (mtDNA) damage and mutations accumulate with age (6, 27-29), mitochondrial damage and reactive oxygen species generation may act as catalysts for age-related degenerative disease, such as coronary artery disease (CAD). It was hypothesized that free radicals generated within the endothelial and smooth muscle cell environment mediate mitochondrial damage within these cells, establishing a vicious cycle of further reactive oxygen species generation and mitochondrial damage leading to vascular cell dysfunction.

Coronary atherosclerotic heart disease is the leading cause of death in the Western world. Although there is considerable controversy about the exact sequence of events leading to coronary atherosclerotic heart, there is growing evidence that atherosclerotic lesions result from factors mediated by reactive oxygen species. Macrophages recognize and internalize ox-LDL via "scavenger" receptors, becoming foam cells. Accumulation of these foam cells is associated with long-term changes in vascular physiology, including smooth muscle cell migration and proliferation, synthesis of extracellular matrix proteins, and further endothelial cell dysfunction, all core components of atherosclerotic plaques. Similarly, many of the risk factors for coronary atherosclerotic heart are related to increased reactive oxygen species production (i.e. smoking and hypercholestermia). Within the artery, reactive oxygen species can be induced by metabolic processes (mitochondrial oxidative phosphorylation), cytokine or growth factor activation, macrophage or neutrophil stimulation (inflammatory response), and the reaction of nitric oxide with superoxide to yield peroxynitrite, which in turn, generates singlet oxygen and hydroxyl radicals. Hence, while there are a variety of processes that are important for atherogenesis, reactive oxygen species-mediated mechanisms and their effects are among the most significant.

Numerous studies have implicated the mitochondria as a vulnerable target for reactive oxygen species. The association of the mitochondrial DNA with the matrix side of the inner membrane makes it susceptible to membrane disturbances, and a potential target for electrophiles generated in the membrane. Aside from its close association with the inner membrane and OXPHOS, additional factors which make the mitochondrial DNA sensitive to damage are the lack of protective histone and non-histone proteins, and its limited DNA repair capacity. Previous studies have shown that the mitochondria are susceptible to reactive oxygen species mediated damage, manifested in extensive lipid peroxidation and mitochondrial DNA damage. Specifically, it has been shown that reactive oxygen species treatment of endothelial cells results in preferential mitochondrial DNA damage, decreased mitochondrial DNA transcripts, and mitochondrial OXPHOS dysfunction.

The prior art is deficient in methods of measuring oxidative stress that contributes to atherogenesis. The present invention fulfills this long-standing need and desire in the art.

SUMMARY OF THE INVENTION

The present invention demonstrates that reactive oxygen species mediates mitochondrial damage and dysfunction in human umbilical vein endothelial cells (HUVEC) and human aortic smooth muscle cells (HASMC) in vitro. DNA damage, gene expression, and mitochondrial protein synthesis were assessed in cells treated with $H_2O_2$, peroxynitrite, and $O_2^-$. The mitochondrial DNA in both cell types was more susceptible to acute doses of reactive oxygen species relative to the nuclear DNA, and was associated with a decrease (40%-60%) in mitochondrial encoded polypeptide OXPHOS transcripts (ND2 and Cytochrome b). Mitochondrial protein synthesis was inhibited with peroxynitrite treatment and reactive oxygen species-exposed cells also had significantly decreased ATP levels and mitochondrial respiration (complex II), consistent with the notion that reactive oxygen species impair mitochondrial function. The present invention reveals a link between oxidative mitochondrial DNA damage, altered gene expression, and mitochondrial dysfunction in vitro, thus, demonstrating that oxidative cell injury and mitochondrial damage play a role in vascular dysfunction and atherogenesis.

By virtue of the notion that the mitochondrial DNA is more susceptible to reactive oxygen species-mediated damage, and because increased oxidative stress is believed to play a role in the early events of atherogenesis, the present invention demonstrates that the mitochondrial DNA in aortic tissues destined to become atherosclerotic has increased damage. For this, the levels of mitochondrial DNA damage sustained in aortic tissues from a hypercholestermic mouse model for atherosclerosis (the apolipoprotein E null mouse) were compared to healthy, age-matched control mice. Assessment of DNA damage found that the aortic tissues from the apoE mice had significantly increased mitochondrial DNA damage before and after the development of pathologically detectable lesions (relative to healthy controls). Additionally, mitochondrial DNA damage increased with age in all mice, however, only the apoE mice had significantly increased ($p<0.05$) levels of damage associated with age. By contrast, diet correlated with the level of mitochondrial DNA damage in only the 10 week old c57B1mice, with the western diet associated with increased damage. Finally, it was found that decreased dietary protein was significantly ($P<0.05$) related with decreased mitochondrial DNA damage in the aortas from both apoE and control mice. There were no clear patterns of damage associated with the β-globin locus, a marker of nuclear DNA damage. Histochemical analysis of aortas from each group revealed the presence of atherosclerotic lesions in only the aged apoE mice on chow (4% fat) or western (21% fat) diets. As expected, lipid peroxides and cholesterol levels were significantly increased in the apoE mice relative to age-matched c57B1controls ($p<0.05$). However, lipid peroxide levels did not increase significantly in the apoE on the higher fat western diet compared to the chow diet. Consequently, these data suggest: 1) that mitochondrial DNA damage occurs prior to, or simultaneous with, atherosclerotic lesion development in a mouse model of atherosclerosis in vivo; 2) aortic mitochondrial DNA damage increases with age in vivo, 3) the apoE genotype confers a greater influence upon the level of mitochondrial DNA damage compared to diet, and 4) dietary effects on mitochondrial DNA damage appear greatest in the young c57B1mice. Hence, mitochondrial DNA damage occurs early in atherosclerosis, and may be an initiating event in atherogenesis.

One object of the present invention is to provide methods of predicting coronary atherosclerotic heart disease, and any other oxidative stress-induced disease, based upon the extent of mitochondrial DNA damage or upon related measurement of mitochondrial dysfunction that is the result of mitochondrial DNA damage including changes in mitochondrial protein production, changes in mitochondrial oxidative phosphorylation or changes in mitochondrial ATP production.

In an embodiment of the present invention, there is provided a method of predicting atherosclerosis in an individual at risk, comprising the steps of: (a) collecting tissue of interest from the individual; (b) determining the amount of mitochondrial DNA (mtDNA) damage in the tissue of interest; and (c) comparing the amount of mitochondrial DNA damage in the tissue of interest from the individual at risk to the amount of mitochondrial DNA damage in tissue of interest from a control individual who does not have atherosclerosis; wherein a greater amount of mitochondrial DNA damage in the individual at risk than in the control individual is predictive of atherosclerosis in the individual at risk.

In another embodiment of the present invention, there is provided a method of measuring the amount of oxidative stress in an individual, comprising the steps of: (a) collecting tissue of interest from the individual; (b) determining the amount of mitochondrial DNA (mtDNA) damage in the tissue of interest; (c) determining the amount of DNA damage in a nuclear gene in the tissue of interest; and (d) comparing the amount of DNA damage per length of DNA between the mitochondrial DNA and the nuclear gene; wherein a greater amount of mitochondrial DNA damage per length of DNA than nuclear DNA damage per length of DNA is indicative of an increased amount of oxidative stress in the individual.

In still yet another embodiment of the present invention, there is provided a method of determining the efficacy of a treatment designed to reduce the risk of coronary artery disease in an individual, comprising the steps of: (a) collecting peripheral white blood cells from the individual prior to treatment; (b) collecting tissue of interest from the individual subsequent to treatment; and (c) determining the amount of mitochondrial DNA (mtDNA) damage in the tissue of interest collected prior to treatment and subsequent to treatment, wherein a decrease in mitochondrial DNA damage subsequent to treatment is indicative of a treatment that reduces the risk of coronary artery disease.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 5A shows a Bar graph depicting the relative levels of MTT reduction. Following exposures, cells were rinsed with PBS and incubated for 1 hour with conditioned medium containing 2.0 µg/ml MTT. Subsequently, medium was removed and cells were lysed, and absorbance measured at 570 nm. MTT reduction (mean±SEM) is reported as a fraction of reduction observed in untreated controls. FIG. 5B shows total ATP determination in HASMC and HUVEC treated with peroxynitrite. Subsequent to treatment, cells were treated with ATP releasing reagent (Labsystems), and ATP levels determined (Molecular Probes) by luminescence. Values are expressed relative to untreated cells (100%).

FIG. 6A shows the QPCR products. Decreased 16.0 kb mtDNA products corresponding to increased damage are observed in 10 and 34 week-old apoE (−/−) aortas compared with age-matched controls. The 16.0 kb (upper row) and 0.08 kb (lower row) products represent long and short QPCR products, respectively. The short QPCR is used to normalize copy number differences between samples (long QPCR/short QPCR). The decreased amplification observed in the apoE (−/−) 16.0 kb QPCR product correlates with increased mtDNA damage.

FIG. 6B shows increased mtDNA damage in 3 week-old apoE (−/−) aortas compared to controls. The 16.0 kb and 0.08 kb products represent long and short mtDNA QPCR products, respectively.

FIG. 7A illustrates the relative amplification of control and apoE mitochondrial DNA m aortas relative to the 24% protein fed control group. Less amplification product signifies increased mitochondrial DNA damage. Asterisks (*) indicate a significant difference between the 24% and 16% protein fed mice. Students t' test P values are in parentheses. FIG. 7B illustrates the relative amplification of control and apoE mitochondrial DNA in the left ventricle relative to the 24% protein fed control group. Less amplification product signifies increased mitochondrial DNA damage. Asterisks (*) indicate a significant difference between the 24% and 16% protein fed mice. Students t' test P values are in parentheses.

In FIG. 10A, whole aortas from hybrid apoE (−/−), SOD2 (+/−) and apoE (−/−) littermates were oil-red-O stained, The upper left panel shows an oil-red-O stained aorta from a 17 week-old apoE (−/−), SOD2 (+/−) male (4% fat diet), and the upper right panel shows the results from an apoE (−/−) male littermate (4% fat diet). Lower left and right panels show stained aortas from 34 week-old apoE (−/−), SOD2 (+/−) and apoE (−/−) littermates, respectively. Black arrows indicate presence of large atherosclerotic lesion in the apoE (−/−), SOD2 (+/−) and apoE (−/−), (not yet present in the 17 week-old apoE (−/−) littermate), and the red arrow in each panel point to an example of smaller lesion formed at arterial branches, that were more frequent and characteristics of the apoE (−/−), SOD2 (+/−) mice. FIG. 10B is a bar graph depicting atherosclerotic lesion frequencies from apoE (/), SOD2 (+/−) and apoE (−/−) mice whole aortas, visualized by oil-red-O staining (n=4).

DETAILED DESCRIPTION OF THE INVENTION

Figure 1A:
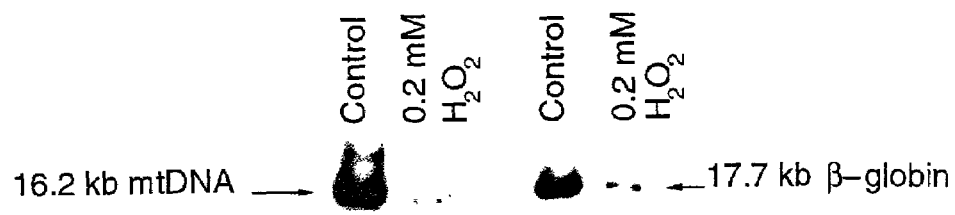
FIG. 1A shows an example of DNA damage associated with hydrogen peroxide treatment in HUVEC. Cells were treated for 60 minutes with 0.2 mM $H_2O_2$, harvested, and QPCR performed. Control cultures were incubated in serum-free medium alone. Less product indicates increased template damage.

Reactive oxygen species have been suggested to play a critical role in the pathogenesis of atherosclerotic lesions, but the underlying mechanisms have not yet been elucidated. Within the vascular environment, superoxide ($O_2^-$) reacts with nitric oxide and diffusion limited rates to form peroxynitrite (peroxynitrite), or alternatively, can be reduced by the enzyme superoxide dismutase to form hydrogen peroxide ($H_2O_2$). Consequently, both $H_2O_2$ and peroxynitrite are relevant reactive oxygen species for study in vascular systems. The present invention demonstrates that hydrogen peroxide and peroxynitrite mediate mitochondrial damage and dysfunction in human umbilical vein endothelial cells (HUVEC) and human aortic smooth muscle cells (HASMC), and thus, contributes to the initiating events of atherogenesis. Cells were treated with $H_2O_2$ and peroxynitrite, and DNA damage, gene expression, and protein synthesis were assessed. Mitochondrial DNA (mtDNA) was preferentially damaged relative to the β-globin gene cluster, a transcriptionally inactive nuclear gene, and this damage was associated with a dose dependent decrease (40%-60%) of mitochondrial DNA encoded OXPHOS gene transcripts. Mitochondrial protein synthesis was slightly inhibited (10%) by 0.1 mM peroxynitrite treatment, and substantially decreased (55%-70%) by 0.5 mM peroxynitrite treatment. Reactive oxygen species treatment also resulted in decreased cellular ATP levels and mitochondrial respiration (complex II, succinate dehydrogenase), consistent with the notion that reactive oxygen species mediate mitochondrial dysfunction. These results provide a link between mitochondrial DNA damage, gene expression, and mitochondrial dysfunction, and thus, provide a paradigm for studying vascular cell dysfunction and atherogenesis.

DNA damage was also evaluated from aortic tissue in 10 and 34 week old atherosclerotic (apoE) and control mice. ApoE mice lack apolipoprotein E, a high affinity ligand for lipoprotein receptors, which are important for LDL uptake from the bloodstream. Consequently, these mice have significantly elevated levels of serum cholesterol and triglycerides, and begin to develop atherosclerotic plaques by 20 weeks of age. To determine the level of nuclear and mitochondrial DNA damage from aortas in each group, genomic DNA was extracted from proximal and distal aortas and subjected to quantitative PCR (QPCR). The apoE mice had increased mitochondrial DNA damage compared with the c57B1control mouse aortas in all groups, except the 10 week, western diet group. Whereas mitochondrial DNA damage increased with age in all mice, only the apoE mice had significantly increased (p<0.05) levels of mitochondrial DNA damage associated with age. The western diet correlated with increased mitochondrial DNA damage (relative to the chow diet) in only the 10 week old c57B1mice. By contrast, there were no significant differences observed in the nuclear DNA (β-globin). In addition, lipid peroxides and cholesterol levels were significantly increased in the apoE mice relative to age-matched c57B1controls (p<0.05), and histochemical analysis of aortas revealed the presence of atherosclerotic lesions in the aged chow and western diet apoE groups. These data suggest: 1) mitochondrial DNA damage is associated with atherogenesis in a mouse model of atherosclerosis in vivo; 2) aortic mitochondrial DNA damage increases with age in vivo, 3) the apoE genotype confers greater influence upon the level of mitochondrial DNA damage compared to diet; and, 4) dietary effects on mitochondrial DNA damage appear greatest in the young c57B1mice. Hence, mitochondrial DNA damage appears to be an initiating event in atherogenesis.

The present invention is directed towards methods of predicting coronary atherosclerotic heart disease based upon the levels of mitochondrial DNA damage. More specifically, the present invention is directed to a method of evaluating the atherosclerotic state of an individual, comprising the steps of (a) collecting tissue of interest from said individual; (b) determining the amount of mitochondrial DNA damage in said tissue of interest; and (c) comparing the amount of mitochondrial DNA damage in tissue of interest from said individual to the amount of mitochondrial DNA damage in tissue of interest from a control individual who does not have atherosclerosis, wherein a greater amount of mitochondrial DNA damage in said individual at risk than in said control individual is indicative of atherosclerosis in said individual. Although the mitochondrial DNA damage may be determined using any technique known to those having ordinary skill in this art, quantitative PCR is one example. This method may be used to identify and quantitate the level of mitochondrial DNA damage of any individual. Preferably, the individual tested has at least one risk factor associated with atherosclerosis. Such risk factors are well known in the art, e.g., tobacco smoking or chewing, hypertension, diabetes, obesity, hypercholesterolemia and hyperlipedemia.

The present invention is also directed to a method of measuring the amount of oxidative stress in an individual, comprising the steps of: (a) collecting tissue of interest from said individual; (b) measuring the amount of mitochondrial DNA damage in said tissue of interest; (c) determining the amount of DNA damage in a nuclear gene in said tissue of interest; and (d) comparing the amount of DNA damage per length of DNA between said mitochondrial DNA and said nuclear gene, wherein a greater amount of mitochondrial DNA damage per length of DNA than nuclear DNA damage per length of DNA is indicative of an increased amount of oxidative stress in said individual. The nuclear gene is selected from the group consisting of the β-globin locus, transcription active or inactive genes, depending upon whether it is also desirable to measure nuclear DNA damage in actively transcribed genes or from a group of nuclear genes. The mitochondrial DNA damage and DNA damage to said nuclear gene may be determined by quantitative PCR. Generally, increased amounts of oxidative stress are predictive of atherogenesis, hypertension, diabetes mellitus, hypercholesterolemia, cigarette smoking, degenerative diseases of aging and cancer.

The present invention is also directed to a method of determining the efficacy of a drug to reduce the risk of atherosclerosis in an individual, comprising the steps of: (a) collecting tissue of interest from said individual prior to and subsequent to administering said drug to said individual; (b) determining the amount of mitochondrial DNA damage in said tissue of interest collected, wherein a decrease in mitochondrial DNA damage subsequent to said treatment is indicative of a treatment that reduces the risk of atherosclerosis.

As used herein, the term "atherogenesis" or "atherosclerosis" refers to the biological process that leads to plaque formation, stenosis and occlusion of peripheral, coronary or cerebral arteries, leading to ischemia, myocardial infarction, stroke and resulting morbidity and mortality.

"As used herein, "tissue of interest" refers to any hematopoietic cell or tissue sample As used herein, the term "oxidative stress" refers to pathophysiological effects of reactive oxygen species, such as $H_2O_2$, superoxide, peroxynitrite, all derivatives of these and other reactive oxygen species, on normal cellular function. The target of oxidative stresses may be proteins, antigens, lipids, RNA, DNA or any other cellular component.

As used herein, the term "antioxidant treatment" refers to any organic or inorganic substances that interact with reactive oxygen species to nullify their pathophysiological effects.

As used herein, the term "low protein diet" generally refers to a diet containing less than 16% protein, but may be adjusted according to the amount of protein contained in the test diet.

As used herein, the term "MtDNA damage" generally refers to any type of lesion (i.e. base alterations, apurinic sites, strand breaks, adduct formation, etc.) or mtDNA length mutation (deletions, insertions, and duplications) that can potentially be detected either directly by QPCR (by blocking the polymerase, or resulting in a QPCR product of size different than anticipated, i.e. mtDNA length mutations), or in concert with an enzymatic action (i.e. DNA can be treated with FAPY glycosylase before QPCR to detect 8-oxo-G)."

A person having ordinary skill in this art would recognize that measurement of mitochondrial DNA damage is only one potential method to determine oxidative stress. Any "downstream" or resultant effect of mitochondrial DNA damage will reflect the same disease process. For example, measurement o f mitochondrial protein production, changes in mitochondrial oxidative phosphorylation or changes in mitochondrial ATP production would accomplish the same goal.

The following examples are given for the purpose of illustrating various embodiments of the invention and are not meant to limit the present invention in any fashion:

EXAMPLE 1

In Vitro Cells and Mice

Human umbilical endothelial vein cells (HUVEC) and human aortic smooth muscle cells (HASMC) were maintained a t 37° C. and 5% $CO_2$/95% air in Dulbecco's Modified Eagles Media (HASMC; Cell Gro) or M199 (HUVEC:Cell Gro) supplemented with 10% (HASMC) or 20% (HUVEC) heat inactivated fetal calf serum (Gibco/BRL), HEPES buffer (10 mM), glutamine, penicillin, and streptomycin. Flasks were routinely split every 3-4 days and disassociated for experiments using trypsin-EDTA (Gibco/BRL). Cells were treated with the various reactive oxygen species (controls mock treated with serum-free media) at 70-80% confluence, between passages 5-7.

The apolipoprotein E (apoE) knockout (–/–) mouse has proven to be a reliable model for development of atherosclerosis. The apoE (–/–) mouse lacks apolipoprotein E, a high affinity ligand for lipoprotein receptors, which are important for LDL uptake from the bloodstream. Consequently, these mice have significantly elevated levels of serum cholesterol and triglycerides, and begin to develop atherosclerotic plaques by 20 weeks of age when fed a "western" high fat diet. Of the mouse models of atherosclerosis, the apoE (–/–) model most closely resembles human atherogenesis.

C57 control and apoE (c57B1background) mice were purchased (Jackson Laboratories, Bar Harbor) at 5 weeks of age, allowed to acclimate to the UTMB Animal Research Facilities for one week, and then fed either a chow (4% fat: Harlan Teklad diet 7001) or western (21% fat: Harlan Teklad #88137) diet commencing at 6 weeks of age for 4 (younger, 10 week old group) or 28 (older, 34 week old group) weeks before tissue collection. For the protein diet experiments, 6 week old mice were fed either 16% (16% protein, 4% fat: NIH31 #101034) or 24% (24% protein, 4% fat: Harlan Teklad diet #7001) protein diets for 4 weeks (10 weeks of age at sacrifice). Each group consisted of 4 apoE and 4 c57B1control mice. Tissues were collected subsequent to intraperotineal injection of ketaset/xylasine (1 mg/20 g). One aorta from each group was used for histochemical analysis, while the remaining proximal and distal aorta, heart, liver, lung, and brain samples were dissected, immediately frozen in liquid nitrogen, and stored at –80° C. until use. Plasma samples were taken and used for determination of total cholesterol (Boehringer Mannheim, Indianapolis, Ind.) and lipid peroxide levels (Calbiochem-Novabiochem, La Jolla, Calif.). Hybrid apoE (–/–)_, SOD2 (+/–) animals were generated by crossing heterozygous SOD2 (+/–) knockout and homozygous null apoE (–/–) mice ($F_0$). F1 double heterozygotes were backcrossed with apoE (–/–) mice to generate appropriate f2 breeders [apoE (–/–), SOD2 (+/–)]. Genotypes were determined through PCR analysis of tail-clips. The SOD2 knockout mouse has been previously characterized; SOD2 (+/–) mice were used as breeders because the SOD2 (–/–) homozygous animal dies within two weeks of birth (62).

EXAMPLE 2

Reactive Oxygen Species Treatments

Concentrated $H_2O_2$ stock (30%, Fisher) was diluted into phosphate buffered saline (PBS) and the concentration determined by absorbance at 230 nm (30). peroxynitrite was synthesized from sodium nitrite and acidified $H_2O_2$ and quantified (31). Xanthine oxidase/lumazine and spermine NONOate were used as low dose $O_2^-$ and nitric oxide donors, respectively. SIN-1 (3-morpholinosydnonimine, hydrochloride, Molecular Probes) was used to generate higher, equimolar levels of nitric oxide and $O_2^-$. Monolayer cultures in 60 mm plates (70%-80% confluent) were exposed to specific reactive oxygen species concentrations for dose response, and time-course experiments in serum-free, phenol red free minimum essential media (MEM) at 37° C. Control monolayers were mock-treated with serum-free and phenol red-free MEM alone. After treatment, cells were washed once with PBS and harvested immediately.

EXAMPLE 3

Quantitative PCR (QPCR) Assay

The QPCR assay measures the average degree of DNA damage per strand for the two template strands in the genomic segment of interest. Detection of DNA damage by QPCR works on: (1) The premise that any DNA template containing a lesion will stop a thermostable polymerase either directly (25, 32), or, in concert with enzymatic action prior to QPCR (i.e. treatment of samples with FAPY glycosylase will enable detection of 8-oxo-G lesions using QPCR), and, (2) Length mutations (deletions and insertions) will alter the size of the expected QPCR product, leading to decreased yield of the expected QPCR product (i.e. mtDNA deletions will result in QPCR products of sizes smaller than the expected product). Consequently DNA lesions (i.e. strand breaks, base modifications, DNA adducts, and apurinic sites), and length mutations (i.e. mtDNA deletions), will either block progression of the polymerase (i.e. lesions)

or yield PCR products of altered size (i.e. mtDNA deletions), leading to decreased amplification of the target sequence (expected size). Therefore only those DNA templates that do not contain DNA length mutations and/or detectable DNA lesions will yield the expected amplification product. Damage is assessed in the mitochondrial genome by amplifying a 16.2 kb product from the mitochondrial DNA template, and the nuclear genome by a 17.7 kb product from the β-globin gene cluster. Increased DNA damage is associated with decreased yields in amplification products. Because differences in QPCR amplifications may at times be related to template copy number differences or simply due to the DNA quality unrelated to in vivo or in vitro mediated damage, a quantitative amplification of a small region is performed as a quality control (32). Small target regions in the DNA are unlikely to suffer any insult, and thus, can serve as indicators of relative copy number and PCR quality of the genomic extract.

Alternative means for quantifying the QPCR products may also be used; these would include fluorescence, luminescence, radioisotope, and immunologic means (antibodies). Examples o f this would be the use of fluorogenic probes labeled with quencher and/or reporter dyes, labeled antibodies or oligonucleotide probes, binding technologies (i.e. biotinylated probes), etc. This type o f quantitative PCR assay alleviates the need for electrophoresis and phospho-imaging. Finally, single-stranded QPCR utilizing the aforementioned methods of quantitation may also be used as a means for quantifying damage to specific strands of DNA.

EXAMPLE 4

DNA Isolation and QPCR

Total cellular DNA was isolated with the Qiagen genomic tip 20G kit as described by the manufacturer. DNA isolation by this technique results in genomic preparations suitable for long QPCR. Total cellular DNA concentrations were determined by ethidium bromide fluorescence with an A4-filter fluorimeter with an excitation band pass filter at 360 nm and an emission cut-off filter at 600 nm (Optical Technology Devices, Elmsford, N.Y.) using λ-HindIII DNA as a standard. Initially, DNA quality was assessed by pulse field electrophoresis prior to QPCR. Sample quality was also tested by QPCR of a 222 base pair fragment in the mitochondrial DNA and an 84 base pair fragment in the β-globin genes (mitochondrial DNA primers: 14619FOR; 14841REV; β-globin primers: 48550FOR; 48634REV), with the expectation that equal template concentrations should yield similar QPCR product (short) concentrations. In experiments with mice, sample quality was tested by QPCR of an 80 base pair fragment in the mitochondrial DNA and an 143 base pair fragment in the β-globin genes (mitochondrial DNA primers: sense 13281-13306, antisense 13335-13361; β-globin primers: sense 21582-21605, antisense 21704-21725).

QPCRs were performed in a GeneAmp PCR system 2400 with the GeneAmp XLPCR kit (Perkin-Elmer). Reaction mixtures contained 15 ng genomic DNA as template. The reagent conditions for the QPCR have been described (25, 32) for the 16.2 kb mitochondrial DNA product (sense primer coordinates: 15149-15174; antisense primer coordinates: 14841-14816, and 17.7 kb b-globin product (sense primer coordinates: 44330-44351; antisense primer coordinates: 61989-61968). Each reaction included 1X XL buffer II (Perkin-Elmer-Cetus), 1.1 mM Mg(OAc)$_2$, 0.1 mg/ml BSA, 0.6 mM primers, 2 mCi α$^{32}$P-dATP (Dupont-NEN), and 1 unit of rTth polymerase (Perkin-Elmer-Cetus). Each QPCR was initiated with a 75° C. hot start addition of the rTth DNA polymerase. In experiments with mice, a quantitative control using one half (7.5 ng) of control genomic template was included in each PCR series to ensure quantitative conditions. After completion of QPCR, 15 μl of each QPCR product was resolved (vertical electrophoresis) on 1% agarose gels (TBE) at 80-90 volts for 4 hours. Dried gels were exposed to phosphor screens for 12-14 hours and quantified with IMAGEQUANT (Molecular Dynamics PhosphoImager 425). Although the use of specific primer locations and placements for QPCR were described, one skilled in the art could logically design many different primer sequences and locations, all depending upon the general approach described in this disclosure.

DNA lesion frequencies were calculated (33). Briefly, the amplification of damaged samples ($A_d$) was normalized to the amplification of non-damaged controls ($A_o$) resulting in a relative amplification ratio ($A_o$ for the 10 and 34-week-old groups was the 10 week-old control group; Ao for the 3 week-old mice was the 3 week-old C57 mice; $A_o$ for the apoE (−/−), SOD2 (+/−) and apoE (−/−) mice was the apoE (−/−) mice). Assuming a random distribution of lesions and using the Poisson equation [$f(x)=e^\lambda \lambda^x/x!$ where λ=the average lesion frequency] for the nondamaged templates (i.e., zero class; x=0), the average lesion frequency per DNA strand was determined; $\lambda=-\ln A_d/A_o$. Statistical analysis was performed using the independent Student's t test. Because no significant differences in DNA damage were observed between the proximal and distal sections of aorta within each respective apoE or c57B1control mouse group using QPCR, the results of each (proximal and distal) were combined per group for intergroup aorta comparisons.

EXAMPLE 5

Northern Transcript Analysis

Control and peroxynitrite treated cultures were harvested with 4M guanidinium isothiocyanate, and total cellular RNA was isolated by centrifugation through 5.7 M cesium chloride (34). For the transcript stability analyses, 2.5 mg/ml of actinomycin D was added prior to addition of peroxynitrite. Heart tissues were solubilized using a polytron tissue solubilizer in 4M guanidinium isothiocyanate. Homogenates were then centrifuged for 15 minutes (3000×g) and supernatents were collected for total cellular RNA isolation by centrifugation through 5.7 M cesium chloride (34). Total RNA was resolved by agarose gel electrophoresis, transferred to nylon membranes, and prehybridized and hybridized (35) to the appropriate probe. Probes for mitochondrial DNA transcripts were made from purified mitochondrial DNA (36) by PCR (16S rRNA: sense primer 2005-2022, antisense 2982-3001; ND2: sense primer 4831-4847, antisense 5464-5481; Cyt b: sense primer 14730-14749, antisense 15845-15863), and gel purified (Qiagen), prior to random $^{32}$P-dCTP labeling (Stratagene). For experiments with RNA extracted from the tissue of mice, gel purified PCR products encompassing portions of the 16SrRNA (sense primer nps 1330-1354; antisense primer nps 2072-2097), ND2 (sense primer nps 4234-4259; antisense primer nps 4916-4941), and Cyt b (sense primer nps 14196-14220; antisense primer nps 14967-14992) genes served as templates for random $^{32}$P-dCTP labeled probes (Stratagene). Filters were exposed to Kodak XAR film at −80° C. The levels of RNA in each sample were normalized by hybridization of β-actin probe supplied commercially (CLONTECH). Autoradiographs were scanned densitometrically (Molecular Dynamics Densitometer SI) and quantitated using IMAGEQUANT (Molecular Dynamics). In regard to the quantitation of mitochondrial transcript levels, any technique used to quantify mtRNA transcript levels would be applicable. Statistical analysis was performed using the independent Student's t test.

EXAMPLE 6

Mitochondrial Protein Synthesis

Methods for mitochondrial protein synthesis analyses have been described (37). Briefly, control and treated cells were washed with methionine-free medium and incubated for 2 hours with 400 mCi/ml of $^{35}$S-methionine in the presence of 100 mg/ml emetine (inhibitor of nuclear protein synthesis), followed by a 20-30 minute chase with 0.1 mM cold L-methionine. Cells were trypsinized, and washed with PBS. Cell pellets were collected, resuspended in solubilizing buffer (4% SDS), sonicated (6 pulses at 30% duty cycle, output 5), and total protein determined. Equal amounts (total protein) of labeled synthesis products were run on 10%-20% gradient PAGE-SDS. Gels were dried onto Whatman filter paper, and exposed to Kodak XAR film at −80° C. The percent labeling of the translation products was determined by densitometry (Molecular Dynamics Densitometer SI) of all bands for untreated and treated samples. The sum of labeling of the bands for each sample was used to calculate the relative levels of incorporation. In regard to the quantitation of mitochondrial protein levels, any technique used to quantify mitochondrial protein synthesis levels would be applicable. Statistical analysis was performed using the independent Student's t test.

EXAMPLE 7

MTT and ATP Assays

Reduction of MTT at complex II was used to assess mitochondrial respiration (38-42). Cells were seeded in 96 well plates at a density of 8,000 cells/well and incubated at 37° C. Forty-eight hours after plating, the medium was replaced with serum-free medium, containing 0.2 mM $H_2O_2$, 0.1 mM, 0.5 mM, or 1.0 mM peroxynitrite for one hour, and allowed to recover in conditioned medium for one hour with MTT at a final concentration of 2.0 mg/ml, lysed, and measured at an absorbance of 570 nm (25). Absorbance values were converted to MTT reduction using a standard curve generated with known numbers of viable cells. MTT reduction for treated samples was then normalized to non-treated control samples and is reported as a fraction of control. Total ATP levels were determined using an ATP determination kit (Molecular Probes, A-6608) and a MicroLumat Plus LB (EG&G Berthold) micro-injector luminometer. Briefly, this assay is based upon luciferin-luciferase bioluminescence (~560 nm) in the presence of ATP. This assay is extremely sensitive; most luminometers can detect as little as 0.1 picomole of pre-existing ATP, or ATP as it is being formed in kinetic systems. Statistical analysis was performed using the independent Student's t test.

EXAMPLE 8

Histological Analysis Lipid Peroxidation and Cholesterol Levers

One aorta from each group was fixed in 4% paraformaldehyde, embedded in paraffin, cut into 5 micron sections, dewaxed, rehydrated, and stained with hematoxylin and eosin, and atherosclerotic lesion development assessed. Alternatively, whole aortas were dissected free from the root to the bifurcation, rinsed in PCS, incised longitudinally, and fixed in a flat position with 10% phosphate-buffered formalin. Fixed aortas were then washed with PBS and stained with oil-red-O (saturated in 60% isopropanol solution), rinsed with 40% ethanol, and washed with PBS.

Lipid peroxidation levels were determined from plasma samples using a colorimetric assay (586 nm; Calbiochem-Novabiochem, La Jolla, Calif.) specific for malonaldehyde (MDA) and 4-hydroxy-2(E)-nonenal (4-HNE), which are end products derived from peroxidation of polyunsaturated fatty acids and related esters. Measurement of such products provides an index of lipid peroxidation. Samples were compared to standard curves of 4-HNE and MDA.

Total cholesterols were determined from mouse plasma samples and a standard curve using a cholesterol determination kit (Boehringer Mannheim, Indianapolis, Ind.) per instructions provided by the manufacturer.

EXAMPLE 9

Results from In Vitro Experiments

Within the vascular environment, superoxide ($O_2^-$) reacts with nitric oxide and diffusion limited rates to form peroxynitrite, or alternatively can be reduced by the enzyme superoxide dismutase to form hydrogen peroxide ($H_2O_2$). Consequently, HUVEC and HASMC were treated with hydrogen peroxide, peroxynitrite, and $O_2^-$ in this series of experiments to demonstrate that hydrogen peroxide and peroxynitrite mediate mitochondrial damage and dysfunction in vitro, and thus, may contribute to the initiating events of atherogenesis.

Hydrogen peroxide treatment resulted in increased mitochondrial DNA damage in both cell lines, while nDNA damage was also sustained in endothelial cells. Both HUVEC and HASMC were treated with 0.2 mM hydrogen peroxide for one hour and assayed for mitochondrial DNA and nuclear DNA (β-globin) damage compared to untreated controls (Table 1, FIG. 1). The mitochondrial DNA and nDNA (β-globin gene cluster) were significantly damaged (compared to untreated samples, P<0.005) in HUVEC while only the mitochondrial DNA sustained significant damage in HASMC (P<0.005). By contrast, HASMC did not show a significant increase in NDNA damage relative to untreated controls (P=0.695).

Figure 1B:
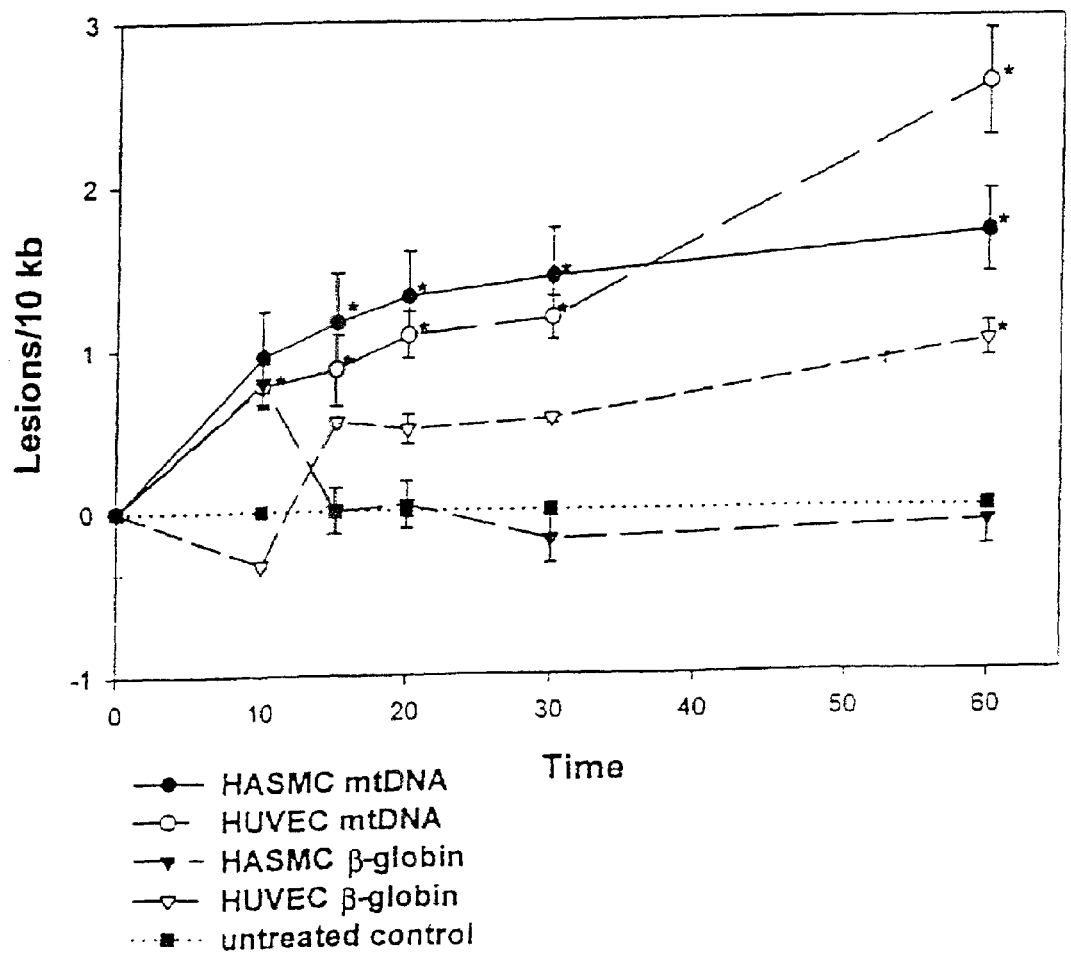
FIG. 1B shows a time-course analyses of $H_2O_2$-treated HASMC and HUVEC cells. Cells were treated with 0.2 mM $H_2O_2$ for 0-60 minutes, genomic DNA extracted, and lesions per 10 kb estimated by comparison with untreated controls (zero class). At least two PCRs per sample were performed for each individual experiment. Asterisks (*) indicate significantly increased ($P<0.05$) damage relative to the untreated control. Symbols represent mean levels (±SEM).

Time course analyses of hydrogen peroxide treatments showed that mitochondrial DNA damage occurred rapidly in both cell lines. Cells were treated with 0.2 mM hydrogen peroxide for 0 -60 minutes, and DNA damage was assessed at each time point (FIG. 1). Significant mitochondrial DNA damage occurred within 10 min in HUVEC (P=0.037) and 15 min in HASMC (P=0.047), compared to untreated controls. By contrast, the β-globin locus did not show a rapid accumulation of nDNA damage (FIG. 1), requiring a 60 min treatment before sustaining significant damage in HUVEC (P=0.005). Consequently, mitochondrial DNA damage occurs rapidly in both HUVEC and HASMC exposed to reactive oxygen species in vitro.

Figure 2A:
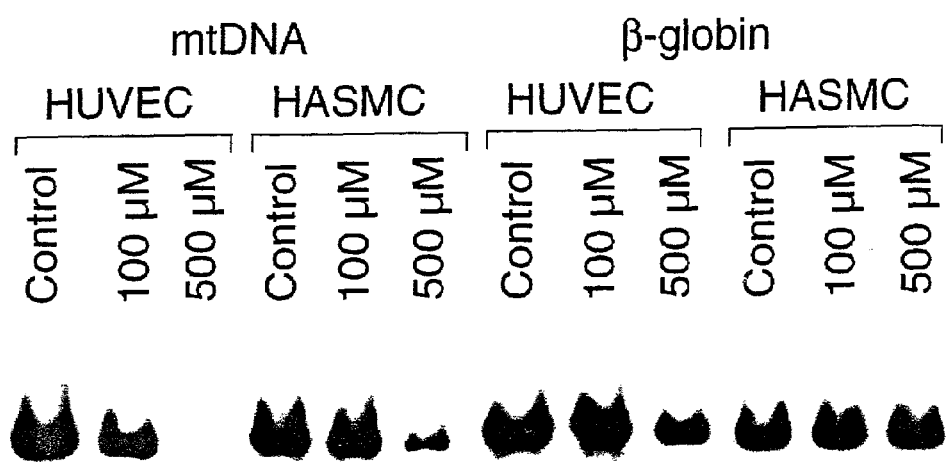
FIG. 2A shows example of DNA damage associated with peroxynitrite treatment in HUVEC and HASMC. Cells were treated for 60 min with the indicated dosages of peroxynitrite, harvested, and QPCR performed. Control cultures were incubated in serum-free medium alone. Less product indicates increased template damage.
Figure 2B:
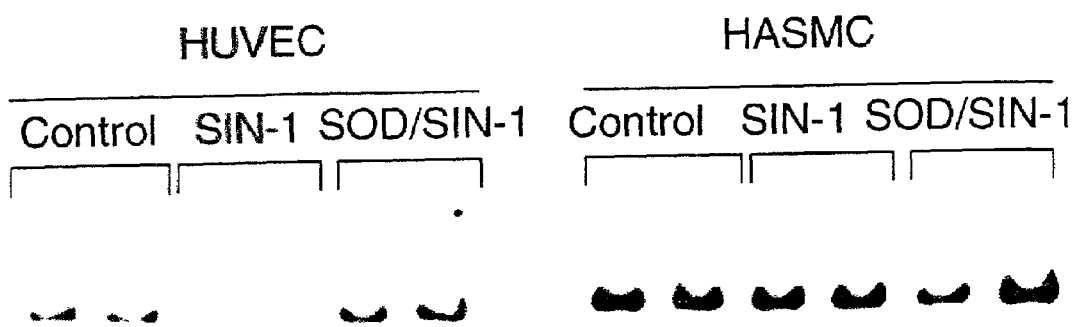
FIG. 2B shows treatment of HUVEC and HASMC with 1 mM SIN-1. SIN-1 generates equimolar amounts of nitric oxide and $O_2^-$. SOD/SIN-1 samples were pretreated with 3 units/ml of SOD prior to SIN-1 treatment. Less product indicates increased template damage.

Peroxynitrite treatment resulted in preferential damage to the mitochondrial DNA in HUVEC and HASMC. To test the effects of peroxynitrite, cells were treated with 0.1 mM and 0.5 mM peroxynitrite for one hour (Table 1, FIG. 2). Treatment of HUVEC with 0.1 mM and 0.5 mM peroxynitrite resulted in significantly increased mitochondrial DNA damage (P<0.005), while 0.5 mM peroxynitrite caused significant mitochondrial DNA damage i n HASMC (P<0.005) relative to untreated samples in all cases (Table 1).

In an effort to evaluate the effects of sustained low dosages of peroxynitrite in vitro, HUVEC and HASMC were treated with $O_2^-$ and nitric oxide donors (reaction of $O_2^-$ with nitric oxide yields peroxynitrite). While treatment of HUVEC resulted in significantly increased mitochondrial DNA damage, HASMC were resistant (Table 1, FIG. 2). For example, whereas sustained nitric oxide generation (0.5 mM/ml/min) by spermine NONOate did no t cause DNA damage, treatment with $O_2^-$ (2 mM/ml/minute) caused significant mitochondrial DNA damage (P<0.05) in HUVEC (Table 1), which was prevented by catalase or SOD pretreatment, implying that both $O_2^-$ and hydrogen peroxide formation from $O_2^-$ reduction was, in part, responsible for mediating mitochondrial DNA damage. Moreover, HUVEC subjected to sustained nitric oxide and $O_2^-$ generation (0.5 mM/ml/min and 2 mM/ml/minute, respectively) experienced significant levels of mitochondrial DNA damage (P<0.05) compared to untreated HUVEC (Table 1). Similarly, acute higher dose generation of nitric oxide and $O_2^-$ in equimolar amounts (1 mM SIN-1) resulted in significant (P<0.001) mitochondrial DNA damage to HUVEC but not HASMC (Table 1, FIG. 2). Pretreatment of cells with SOD prevented SIN-1 associated mitochondrial DNA damage in HUVEC (Table 1, FIG. 2). Consequently, sustained low dose and acute high dose production of $O_2^-$ and nitric oxide causes mitochondrial DNA damage in HUVEC.

Figure 3:
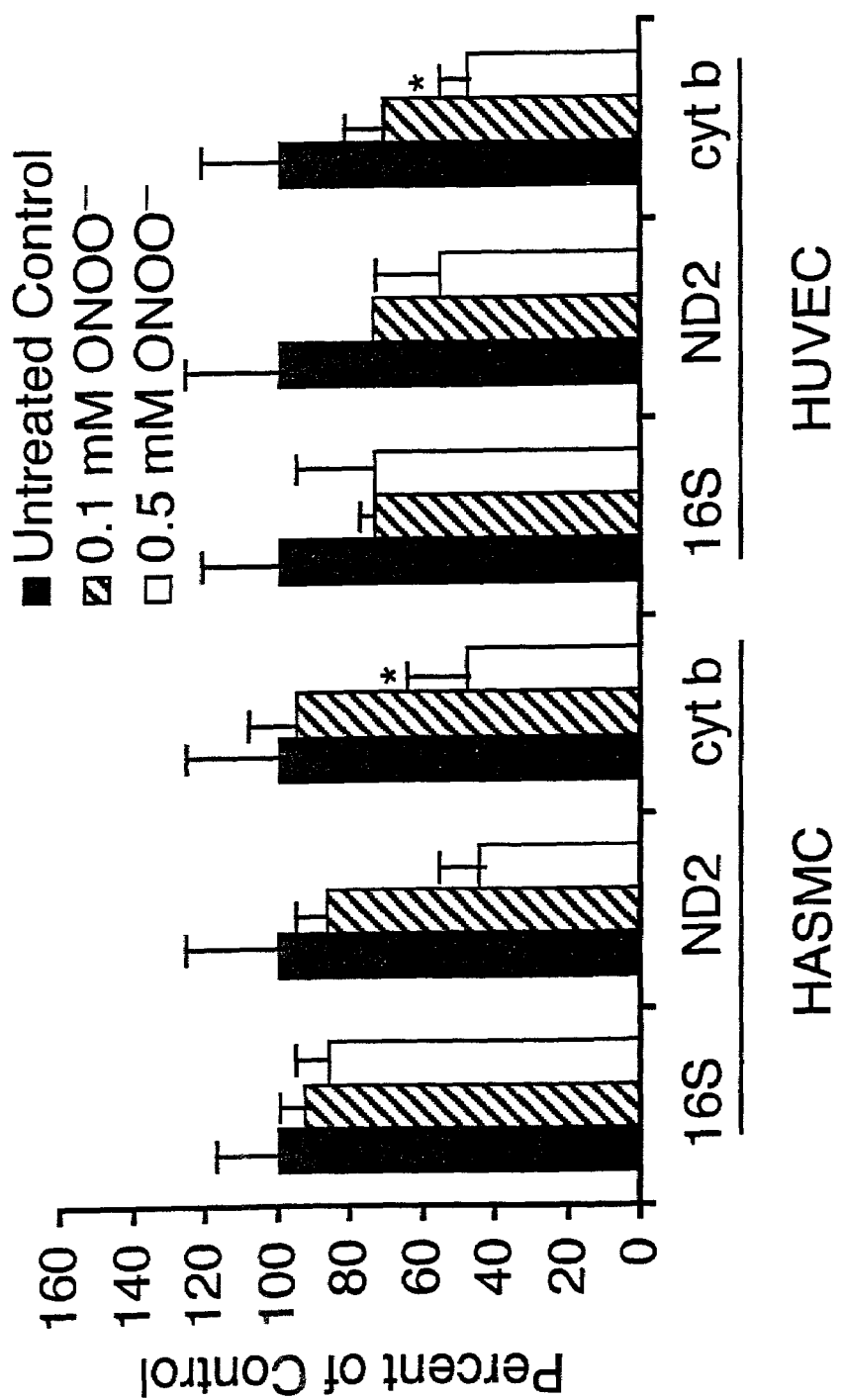
FIG. 3 shows mitochondrial DNA transcript levels in peroxynitrite treated cells. Bar graph representing the relative transcript levels (mean±SEM; normalized by β-actin) of 16S rRNA, ND2, and Cyt b after a 60 min treatment (0.1 mM and 0.5 mM, serum-free media) to untreated controls (serum-free media). Transcript levels were determined by Northern analysis and hybridization to the appropriate radiolabeled probe. Asterisks (*) indicate transcript levels significantly different (P<0.05) from the untreated control.

Treatment of HUVEC and HASMC with peroxynitrite resulted in substantially decreased transcript levels in the mitochondrial encoded genes, NADH dehydrogenase 2 (ND2) and cytochrome b (Cyt b), but not the 16S rRNA. Treatment with 0.5 mM peroxynitrite in HASMC resulted in 55% decrease in ND2 and Cyt b transcript levels, while the 16S rRNA levels were reduced by 14% (FIG. 3). Similarly, HUVEC treated samples had a 45%-50% reduction in ND2 and Cyt b transcripts when treated with 0.5 mM peroxynitrite, while the 16S rRNA levels were decreased by 26% relative to untreated controls (FIG. 3). When a lower dose o f peroxynitrite (0.1 mM) was used, HUVEC 16S rRNA, ND2 and Cyt b transcript levels were reduced 25%-30% while HASMC showed a reduction of 5%-15% (FIG. 3).

Pretreatment of cells with actinomycin D, an inhibitor of transcription, revealed that peroxynitrite treatments caused both transcriptional inhibition (ND2 and Cyt b) and degradation of specific transcripts (Cyt b). By contrast, transcript levels of the nuclear β-actin gene were unaffected by peroxynitrite treatments. Hence, peroxynitrite is capable of differentially affecting both transcription and transcript stability in mitochondrial genes.

Table 1 shows the lesion frequency (per 10 kb) estimated in the mitochondrial DNA and nDNA (β-globin gene cluster) compared to "zero-class" untreated controls when treated with hydrogen peroxide ($H_2O_2$) and peroxynitrite treatments. Degraded peroxynitrite refers to peroxynitrite incubated with media for 1 hour at room temperature before addition (0.5 mM) to cultured cells. Values are expressed in terms of mean (±SEM).

TABLE 1

Estimated Lesions per 10 Kb Following Treatment with Reactive Oxygen Species I

| | Untreated Control | 0.2 mM $H_2O_2$ | 0.1 mM peroxynitrite | 0.5 mM peroxynitrite | Degraded peroxynitrite |
|---|---|---|---|---|---|
| HASMC | | | | | |
| mtDNA | 0 | 1.68 (0.25)** | 0.16 (0.05) | 1.42 (0.35)** | 0 |
| nDNA | 0 | −0.09 (0.14) | −0.08 (0.05) | −0.04 (0.03) | ND |
| HUVEC | | | | | |
| mtDNA | 0 | 2.59 (0.33)** | 0.19 (0.03)** | 2.81 (0.37)** | 0.07 (0.03) |
| nDNA | 0 | 1.02 (0.11)** | 0.07 (0.10) | 1.05 (0.40) | 0.01 (0.05) |

ND = no data.

Figure 4A:
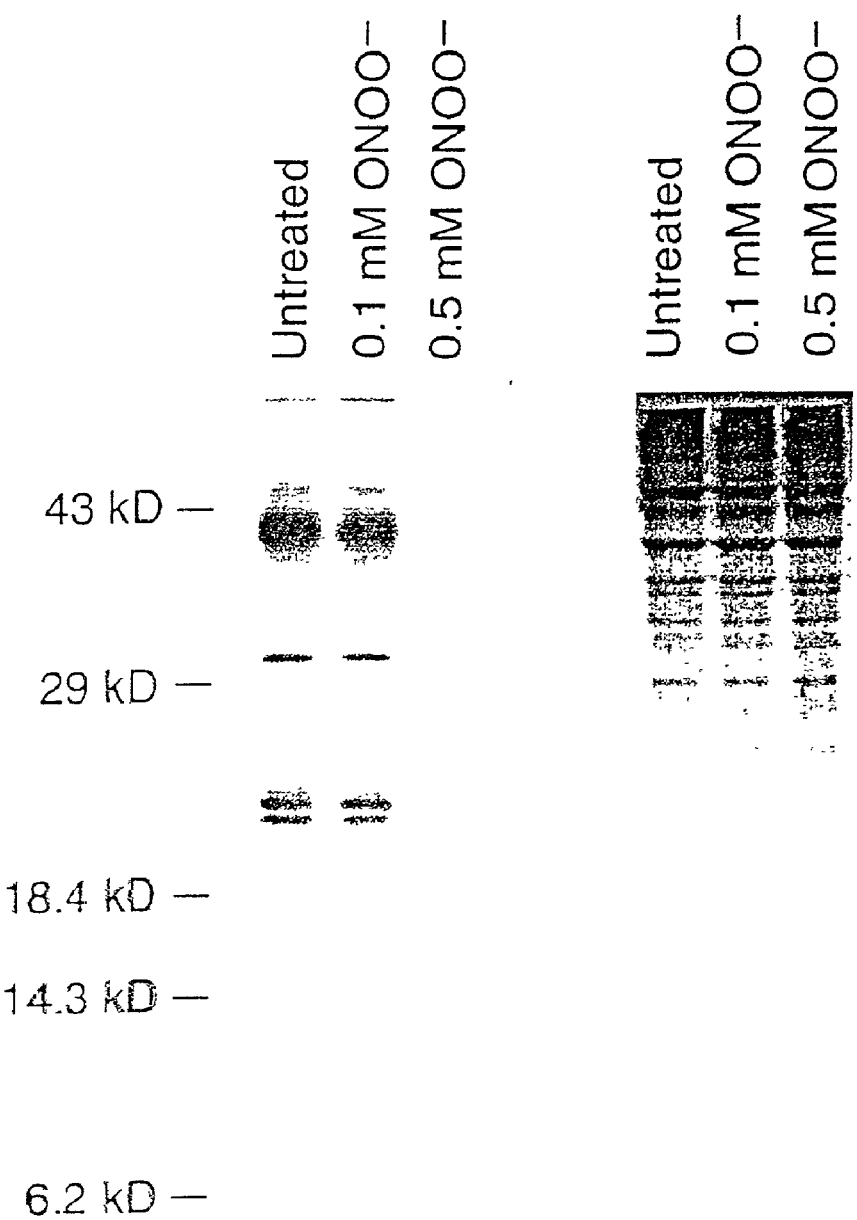
FIG. 4 shows $^{35}$S-methionine incorporation in mitochondrial synthesized proteins subsequent to peroxynitrite treatment in HASMC (left panel). Cells were treated with 0.1 mM or 0.5 mM peroxynitrite for 60 min, and then labeled with $^{35}$S-methionine for ~2 hours before SDS-PAGE electrophoresis. The right panel shows the same gel stained with comassie blue.

Reactive oxygen species treatment also resulted in a decrease in mitochondrial protein synthesis in both cell lines. Treatment of HUVEC and HASMC with 0.2 mM $H_2O_2$ resulted in a 23%-33% decrease in overall mitochondrial protein synthesis, while treatment with 0.5 mM peroxynitrite was associated with a 55%-70% (HUVEC and HASMC, respectively) loss of mitochondrial protein synthesis compared to untreated cells (FIG. 4 and Table 2). Lower doses of peroxynitrite (0.1 mM) in HASMC revealed a slight decrease of 12% in $^{35}$S-methionine incorporation. Hence, reactive oxygen species treatment can also be associated with decreased mitochondrial protein synthesis. Table 2 summarizes the percent $^{35}$S-methionine incorporation in both HUVEC and HASMC treated with reactive oxygen species relative to controls that were mock treated with serum-free media.

TABLE 2

35S-Methionine Incorporation Compared to Control

| | Control | 0.2 mM $H_2O_2$ | 0.1 mM ONOO⁻ | 0.1 mM ONOO⁻ |
|---|---|---|---|---|
| HASMC | 100% | 67% | 88% | 30% |
| HUVEC | 100% | 77% | ND | 45% |

ND = no data.

Figure 5A:
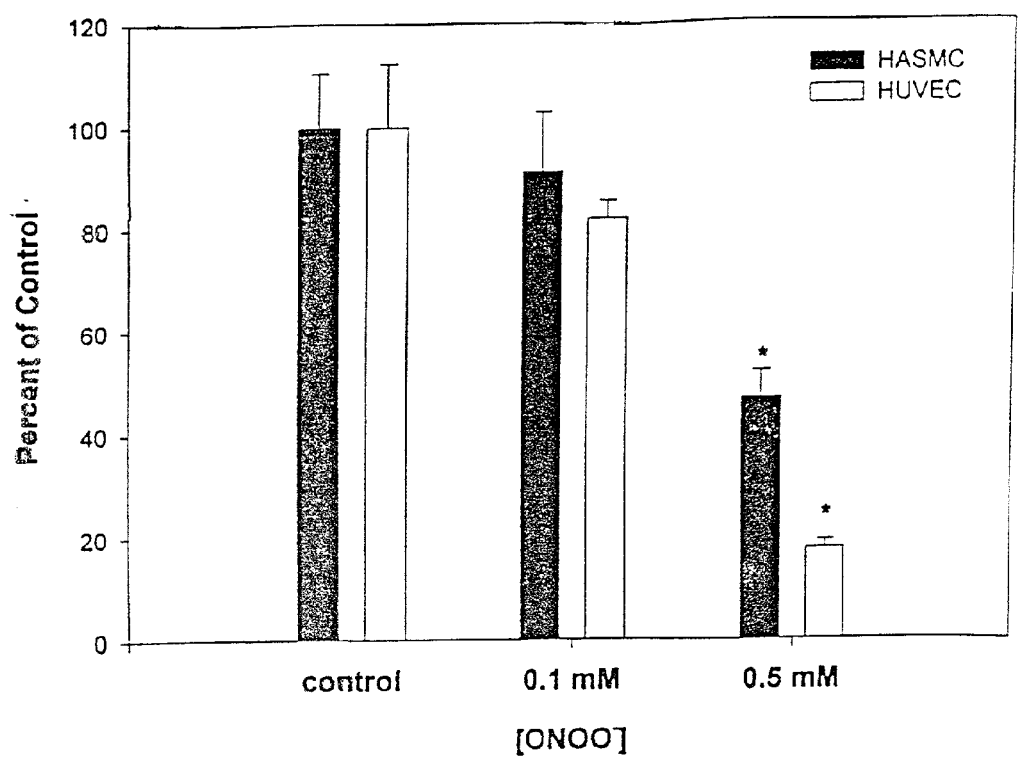
FIGS. 5A and 5B show bar graphs representing mitochondrial respiration (assayed by MTT reduction) and total cellular ATP. HASMC and HUVEC were exposed to the respective concentration of peroxynitrite for 1 hour at 37° C.
Figure 5B:
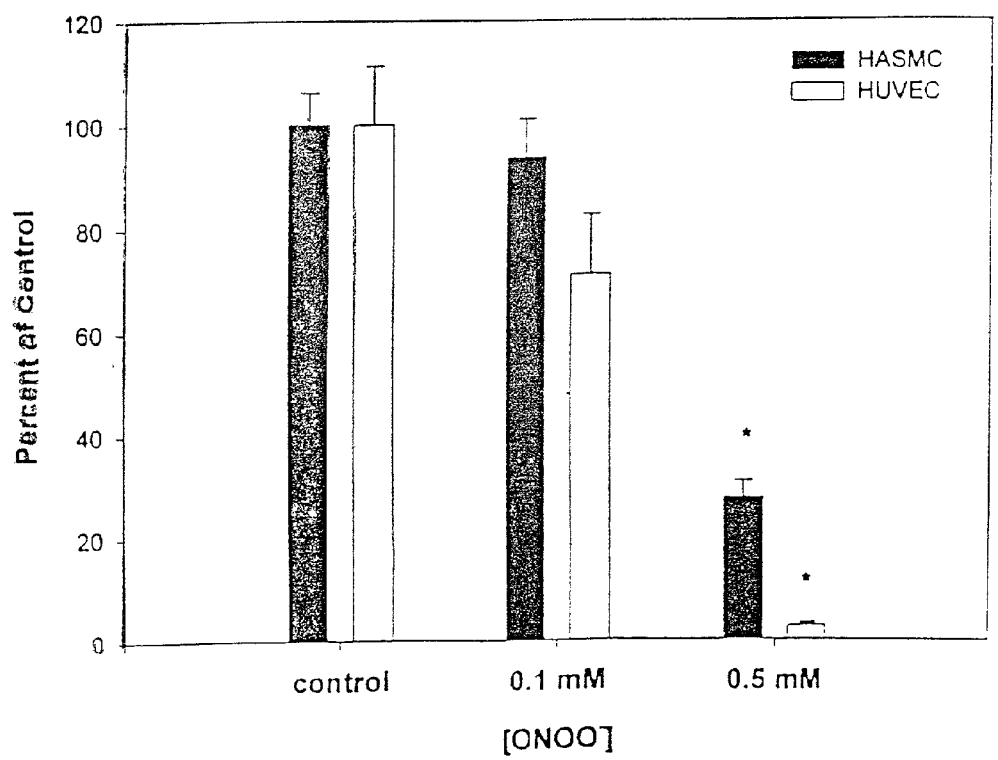

Peroxynitrite treatment also resulted in an overall decrease in ATP levels and mitochondrial respiration (complex II) in HUVEC and HASMC (FIG. 5). Assessment of total ATP levels revealed that while the 0.1 mM dose of peroxynitrite did not result in a significant reduction in total ATP in either cell line, the 0.5 mM dose resulted in significant decreases in ATP (HUVEC, P=0.02; HASMC, P=0.04). Similarly, the 0.1 mM peroxynitrite treatment did not result in a significant decrease of complex II reduction of MTT (mitochondrial respiration), whereas the 0.5 mM dose caused a significant decline (HUVEC, P=0.02; HASMC, P=0.008).

MTT reduction by succinate dehydrogenase, a component of complex II of OXPHOS, is an indicator of mitochondrial function and is often used as a means to assess respiratory and redox function in cells. Consequently, reduction of MTT will reflect mitochondrial redox capacities. In parallel experiments, cells were stained with trypan blue to determine the degree of cell death associated with each reactive oxygen species treatment. Both cell lines had virtually no cell death (<5%) at the times assayed for MTT and ATP. Consequently, reactive oxygen species treatment appears to have an effect on total ATP levels and respiration in HUVEC and HASMC.

Table 3 shows the estimated frequency of lesions (per 10 kb) in the mitochondrial DNA and nDNA (β-globin gene cluster) associated with superoxide ($O_2^-$) and nitric oxide (NO) donors. Xanthine oxidase plus lumazine were used for $O_2^-$ generation (2 mM/ml/min), while spermine NONOate was used to generate nitric oxide (0.5 mM/ml/min). SIN-1 (1 mM) was used to generate equimolar amounts of nitric oxide and $O_2^-$. For the SOD+SIN-1 exposures, cells were pretreated with 3 units/ml SOD before SIN-1 addition. Abbreviations: *significantly different from control (P<0.05); **significantly different from control (P<0.005); nd=no data; a negative value (−) indicates that there was less damage observed compared to the untreated control.

TABLE 3

Estimated Lesions per 10 kb Following Treatment with Reactive Oxygen Species II

|  | Untreated Control | 0.2 mM $O_2$ | 0.1 mM $O_2$ + NO | 0.5 mM SIN-1 | 0.5 mM SOD + SIN-1 |
|---|---|---|---|---|---|
| HASMC |  |  |  |  |  |
| mtDNA | 0 | 0 | 0 | 0.13(0.05) | 0.05(0.15) |
| nDNA | 0 | 0 | 0 | ND | ND |
| HUVEC |  |  |  |  |  |
| mtDNA | 0 | 0.22(0.04) | 0.41(0.04) | 1.71(0.33) | −0.17(0.12) |
| nDNA | 0 | 0 | 0.08(0.11) | ND | ND |

EXAMPLE 10

Mitochondrial DNA Damage in apoE (−/−) Hypercholesteremic Mice

Hematoxylin and eosin-stained sections of aortas from 10 and 34-week-old apoE (−/−) and control (c57BL/J6) mice were examined to determine the extent and distribution of atherosclerotic lesions. The degree and progression of atherosclerosis in the apoE (−/−) mice used in this series of experiments was consistent with previous observations (63, 64). No lesions were apparent in vascular sections from either 10-week-old control or apoE (−/−) mice. In contrast, atherosclerotic lesions were present in 34-week-old apoE (−/−) mice but were absent in age-matched control aortas (data not shown).

Figure 6:
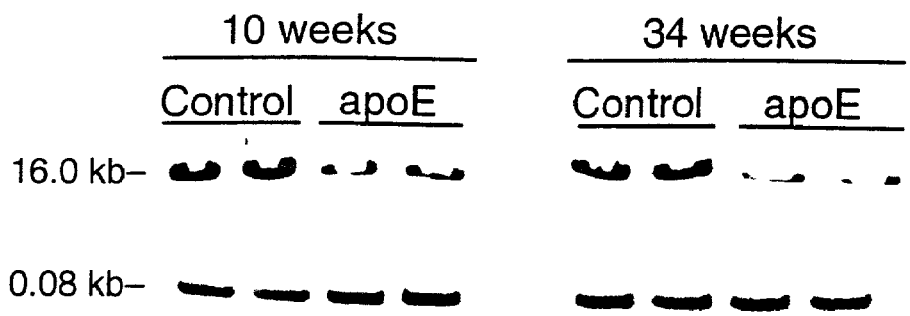
FIGS. 6A and 6B show QPCR of control and apoE (−/−) aortic mtDNA.
Figure 6:
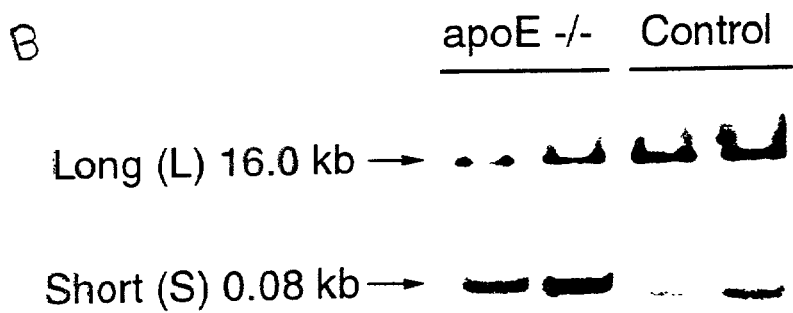

QPCR was used to compare mitochondrial damage in the aortas of the control and apoE (−/−) mice. The QPCR results demonstrate that aortic tissues from apoE (−/−) mice had significantly increased mtDNA damage both before (10 weeks) and after (34 weeks) the development of histologically detectable lesions relative to healthy controls (FIGS. 6A and Table 4). QPCR of 10-week-old apoE(−/−) aortas demonstrated a mean 60.6% decrease in mtDNA amplification (reflecting an increase in DNA lesions) compared with age-matched controls (0.582±0.123 mtDNA lesions/10 kb compared to 0.0±0.198 lesions/10 kb, P=0.018). Similarly, the 34-week-old apoE (−/−) group had a three fold increase in mtDNA damage compared with age-matched controls (1.325±0.257 lesions/10 kb versus 0.453±0.162 lesions/10 kb, P=0.007).

TABLE 4

The Effects of Genotype and Age on mtDNA Damage (Lesions/10 kb) in apoE (−/−) and Control Mice

|  | Age | | P Value | |
|---|---|---|---|---|
|  | 10 Weeks | 34 Weeks |  |  |
| Control | 0.00 (0.20) | 0.45 (0.16) | 0.09 | Effects of Age |
| apoE (−/−) | 0.58 (0.12) | 1.32 (0.26) | 0.0131 | of Age |
| P Value | 0.018 | 0.008 |  |  |
| Effects of Genotype | | | | |

Table 4 summarizes the mtDNA lesions per 10 kb. Values are the mean ± SEM determined from three experiments (n = 6 data points/group/experiment). Estimates are listed for each genotype (control and apoE (−/−)) and age group. Number of mtDNA lesions for each group are expressed relative to the 10 week-old control group, which was designated as the "zero" mtDNA lesion class group (0.0 ± 0.20 lesions/10 kb). Statistical analysis (independent Student's t test) revealed significant differences between control and apoE (−/−) genotypes within each age class (effects of genotype) and between 10 and 34 week-old mice within each genotype (effects of age). DNA lesion frequencies were calculated as previously described (62). Values are expressed as mean ± SEM.

In contrast to the effects of the apoE (−/−) background on mtDNA damage, no statistically significant differences were observed between control and apoE (−/−) groups for damage at the β-globin gene locus [used as a marker for nuclear DNA damage (10-week-old group P=0.187; 34-week-old group; P=0.098)] indicating the increased sensitivity of the mitochondrial genome to damage compared with nuclear DNA.

There was also a measurable effect of age on mtDNA damage in apoE (−/−) mice. Aortic mtDNA damage increase 2.3-fold with age in apoE (−/−) mice as seen in Table 4 (10 week-old versus 34-week-old; P=0.013). Control mice had measurable, but not statistically significant (P=0.088), levels of mtDNA damage during the same time period.

To determine whether aortic mtDNA damage was present prior to the earliest stages of atherogenesis (before inflammatory cell adherence to the vessel wall), aortas from 3 week-old apoE (−/−) and control mice were examined. Aortas from 3 week-old apoE (−/−) mice had significantly higher levels of mtDNA damage compared with age-matched control animals (FIG. 6C and Table 5; P=0.001), confirming that mtDNA damage occurs early in aortas predestined for atherosclerotic lesion development. Hence, these findings indicate that mtDNA damage preceded atherogenesis in apoE (−/−) mice.

TABLE 5

Lesion Frequencies/10 kb in 3-Week-Old Control and apoE (−/−) Aortas

| Control | apoE (−/−) | P value |
|---|---|---|
| 0.0 (0.15) | 1.36 (0.16) | 0.001 |

Table 5 lists the relative lesion frequencies (lesions/10 kb) in the 3 week-old control (zero-class, $A_0$ (33)) and apoE (−/−) aortas. Values are expressed as mean and (SEM).

EXAMPLE 11

Diet and DNA Damage in Mice

Hypercholesteremic apoE (−/−) and "healthy" control mice were divided into two age groups (10 weeks or 34 weeks of age at sacrifice) and fed either chow (4% fat) or western (21% fat) diets commencing at 6 weeks of age. Aortic and heart (left ventricle) tissues were assessed for DNA damage using QPCR, while blood plasmas were used to determine cholesterol and lipid peroxidation (4-HNE and MDA) levels. One aorta from each group was preserved for histological studies.

Aortic tissues from the hypercholesteremic apoE mice fed the chow diet had significantly increased levels of mitochondrial DNA damage compared to controls (P<0.05; data not shown). These differences were observed in both the 10 and 34 week old mice, which clearly showed that apoE aortas sustained greater mitochondrial DNA damage in vivo compared to "healthy" mice. The 10 week old apoE aorta yielded a 61% decrease in amplification (decreased amplification correlates with increased DNA damage) relative to the zero class control, or an estimated 0.582±0.123 mitochondrial DNA lesions/10 kilobases (kb) compared to 0.0±0.198 lesions/10 kb in the 10 week old control mouse (P=0.018). Similarly, the 34 week old apoE roup had a three-fold increase in estimated mitochondrial DNA damage compared to the age matched control group (1.325±0.257 lesions/10 kb versus 0.453±0.162 lesions/10 kb; P=0.007). These same patterns were also observed in tissue of the left ventricle of the heart. (data not shown). For example, the 10 week old apoE mice had a 67% decrease in amplification compared to the zero class control (0.685±0.093 lesions/10 kb versus 0.0±0.048 lesions/10 kb; p<0.001), while the 34 week old apoE mice sustained approximately 4-fold higher estimated mitochondrial DNA lesions compared to the age-matched controls (0.819±0.151 lesions/10 kb versus 0.213±0.295 lesions/10 kb, P=0.056).

The effects of the western diet were also assessed in apoE and control mice. In the control mice, the western diet was associated with higher levels f mitochondrial DNA damage in the 10 week-old control group aortas compared to chow fed control mice (0.31±0.17 lesions/10 kb versus 0.0±0.20 lesions/10 kb, western and chow, respectively), however, this difference was less significant (P=0.25). Such differences were less obvious in the 34 week old control mice (i.e. 0.45±0.16 lesions/10 kb and 0.49±0.25 lesions/10 kb in chow versus western, respectively, P=0.90). Similarly, the 10 week old control mice showed increased estimated mitochondrial DNA damage with the western diet in heart (58% decrease in amplification, 0.54±0.23 lesions/10 kb and 0.0±0.05 lesions/10 kb in western versus chow, respectively), yet similar with the results seen in the aorta, no obvious differences were seen in the 34 week old control mice (0.21±0.29 lesions/10 kb and 0.25±0.21 lesions/kb in chow versus western, respectively). By contrast, no apparent increases in micochondrial DNA damage accompanied the western diet in either aorta or heart tissues from apoE mice. Hence, increased dietary fat appeared to be associated with increased mitochondrial DNA damage in the 10 week old control mice only.

Age was also associated with an increase in mitochondrial DNA damage in both apoE and control mice aortas (Table 6). An estimated 2.3-5.8 fold increase in lesions were observed between the 10 week old and 34 week old apo E mice aortas (chow diet, P=0.013; western diet P=0.011), while the control mice did not have significantly increased levels of damage, but did have substantial increases (Table 6). Increased age appeared to affect the chow fed control mice (0.0±0.20 lesions/10 kb vs. 0.45±0.16 lesions/10 kb, 10 and 34 weeks, respectively, P=0.09) while less difference was seen with age in the western diet fed mice (0.31±0.17 lesions/10 kb vs. 0.49±0.25 lesions/10 kb, 10 and 34 week old, respectively, P=0.556). By contrast, no significant associations were seen in the heart. Hence, age appeared to significantly correlate with increased mitochondrial DNA damage in aorta from apoE mice, while a trend appeared evident in the chow fed control mice.

Figure 7A:
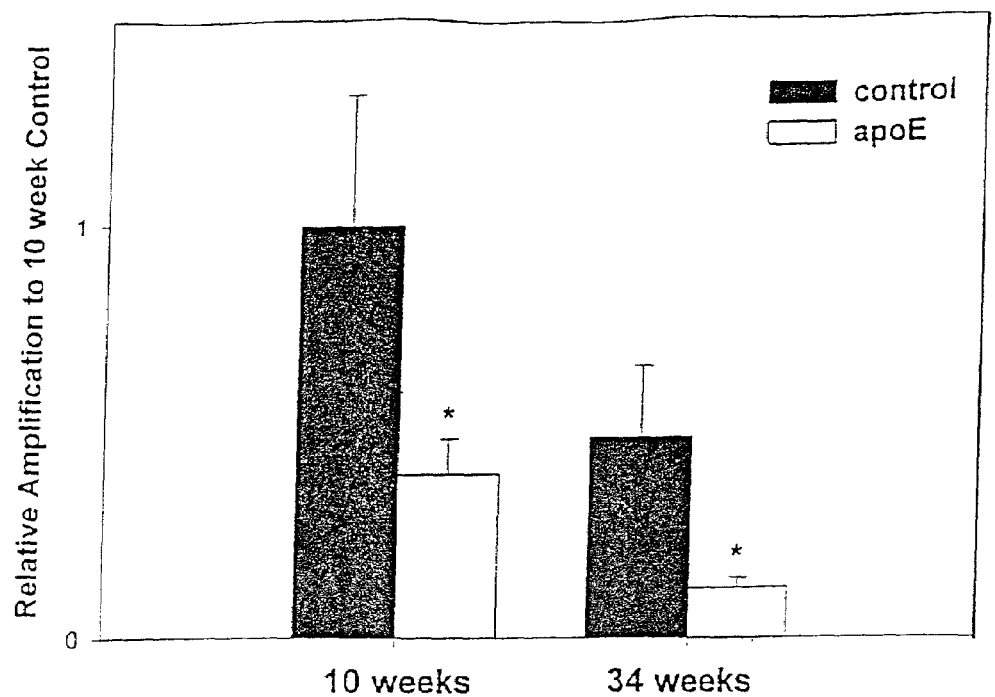
FIGS. 7A and 7B show that decreased dietary protein intake correlates with less mitochondrial DNA damage in control and apoE mice. Control and apoE mice were fed either a 16% or 24% protein diet for 4 weeks, commencing at 6 weeks of age, and mitochondrial DNA damage was assessed by QPCR.
Figure 7B:
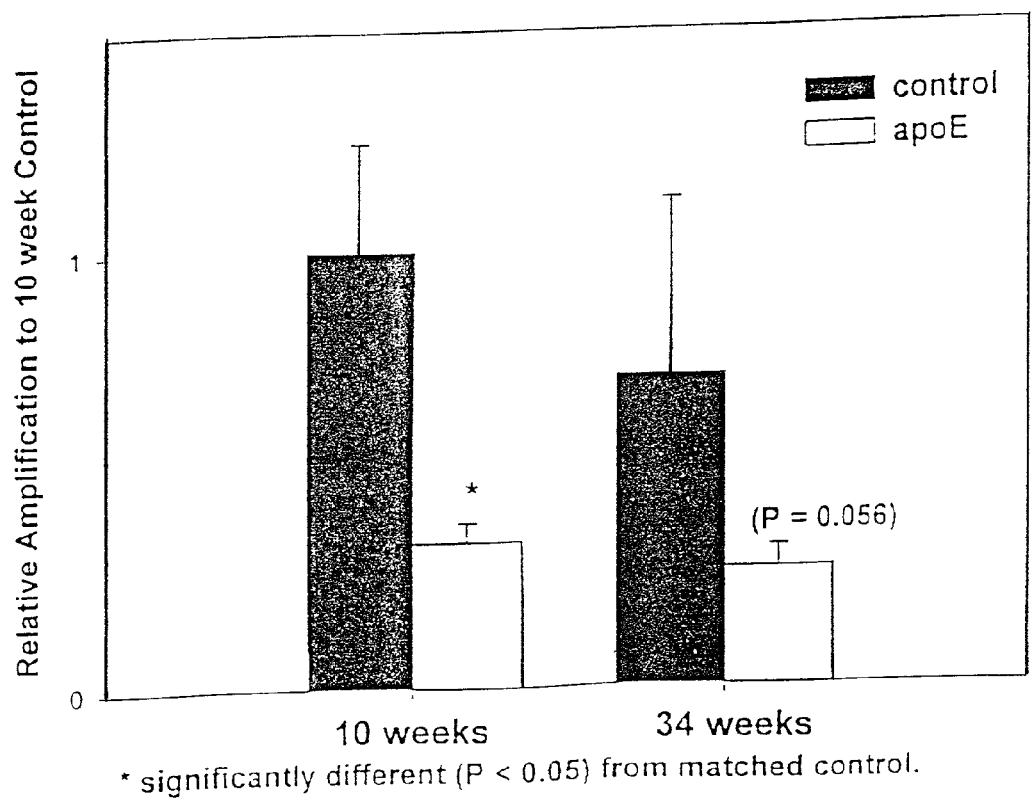

Because no significant differences in mitochondrial DNA damage were observed between the chow and western diets with matched genotype and age, the effects of protein. in the 10 week old mice were investigated. Both apoE and c57B1control mice were fed either 16% or 24% protein diets for 4 weeks, commencing at 6 weeks of age. While both diets resulted in apoE still having greater levels of mitochondrial DNA damage compared to controls (aorta P=0.015; heart P=0.005), the lower protein diet resulted in a significant decrease in damage in both control (P=0.007) and apoE (P<0.001) in aorta (FIG. 7). This same trend was also observed in apoE heart (P=0.002). Hence, the lower protein diet was associated with decreased mitochondrial DNA damage in both types of mice.

TABLE 6

The effects of age on mtDNA damage (lesions/10 kb) in atherosclerotic (apoE) and control (C57) mice

| Diet | Mouse | 10 weeks of age | 34 weeks of age | P value |
| --- | --- | --- | --- | --- |
| 4% fat | Control (C57) | 0.00 (0.20) | 0.45 (0.16) | 0.009 |
|  | ApoE | 0.58 (0.12) | 1.32 (0.26) | 0.013 |
| 21% fat | Control (C57) | 0.31 (0.17) | 0.49 (0.25) | 0.56 |
|  | ApoE | 0.15 (0.11) | 0.88 (0.25) | 0.01 |

Table 6 lists the estimated [mean (SE)] mtDNA lesions per 10 kb relative to the 4% fat, control group (C57). All diets were commenced in mice at 6 weeks of age, and continued until either 10 or 34 weeks of age. The students t' test was used for statistical analysis. The estimated lesion frequencies per 10 kb of mitochondrial DNA relative to the 10 week old c57B1chow fed control (zero class lesions). Data are listed as mean (± SEM). Students t' P values are given comparing the10 vs. 34 week old group for each genotype (apoE or c57) and diet. Asterisks (*) indicate a significant difference from the 10 week counterpart.

EXAMPLE 12

Cholesterol Levels in Mice

As expected, cholesterol levels were significantly elevated among all the apoE groups compared to control mice (~4 to 5-fold higher; P<0.001). While the western diet was associated with the highest cholesterol levels in all mice, these increases (relative to the chow diet,) were significant in apoE mice only (~2.2-fold higher; chow, 225.8±33.4 mg/dl; western, 490.2±56.7 mg/dl; P=0.0019). By contrast, the c57B1control mice experienced slightly higher cholesterol levels (~1.6-fold higher; chow, 53.4±15.1 mg/dl; western, 85.2±10.8 mg/dl) on the western diet, but not significantly higher (P=0.17). Hence, the apoE mice had significantly higher levels of cholesterol compared to the age-matched c57B1controls, and the highest cholesterol levels were associated with the western diet.

EXAMPLE 13

Lipid Peroxides in Mice

Figure 8A:
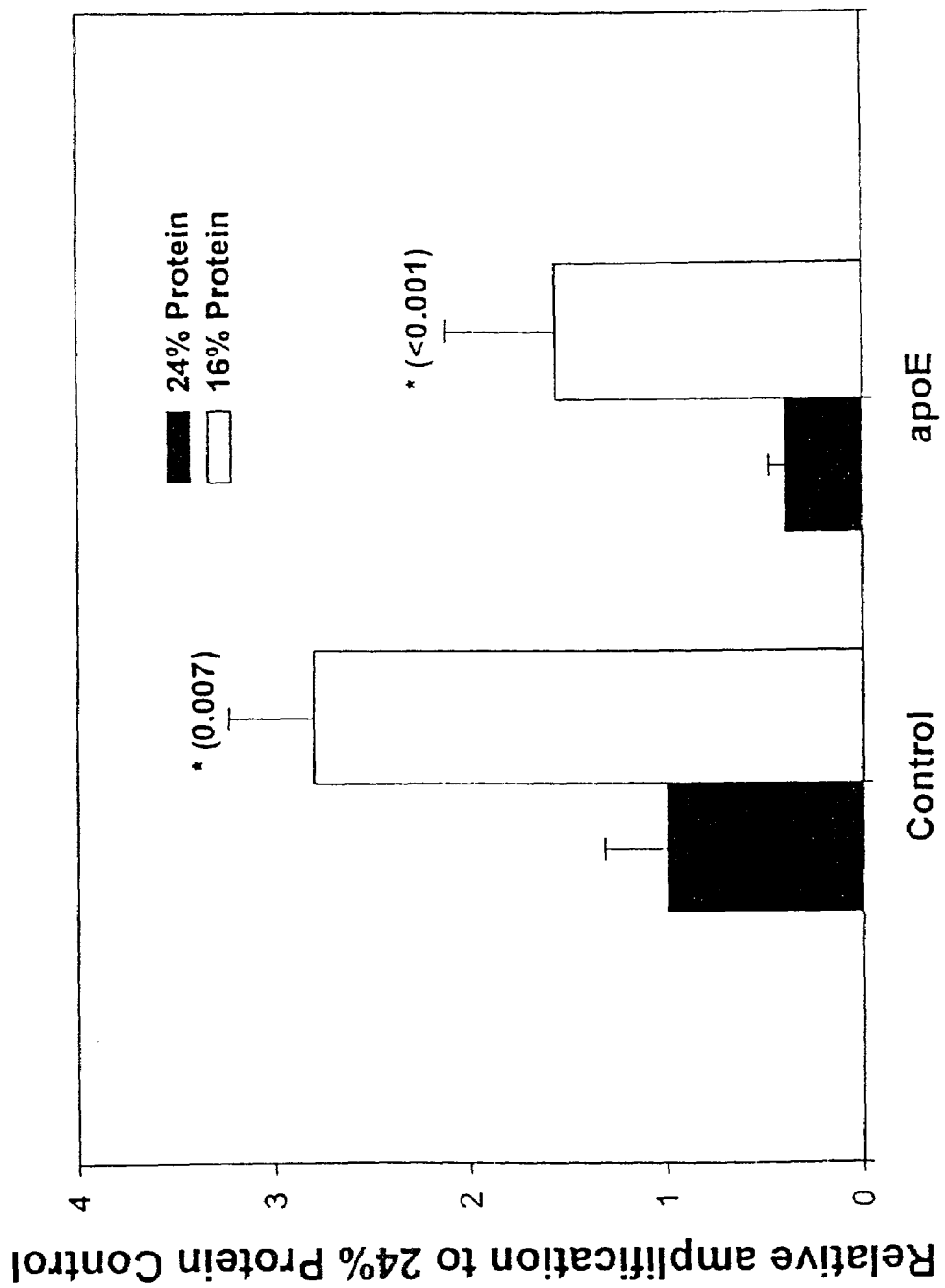
FIG. 8 shows that lipid peroxidation is significantly increased in apoE compared to control mice, but lipid peroxidation is significantly increased in control mice fed the western (21% fat) diet. Bar graph illustrates the level of lipid peroxidation in apoE and control mice fed chow (4% fat) or western (21%) diets. Values are expressed relative to the chow fed control mice. While apoE had significantly higher levels of lipid peroxidation compared to control mice regardless of diet, there were no significant differences in the level of lipid peroxidation among the apoE fed the chow or western diets. By contrast, the control mice fed the western diet had significantly higher levels of lipid peroxidation (indicated by "*") compared to control mice fed the chow diet.
Figure 8B:
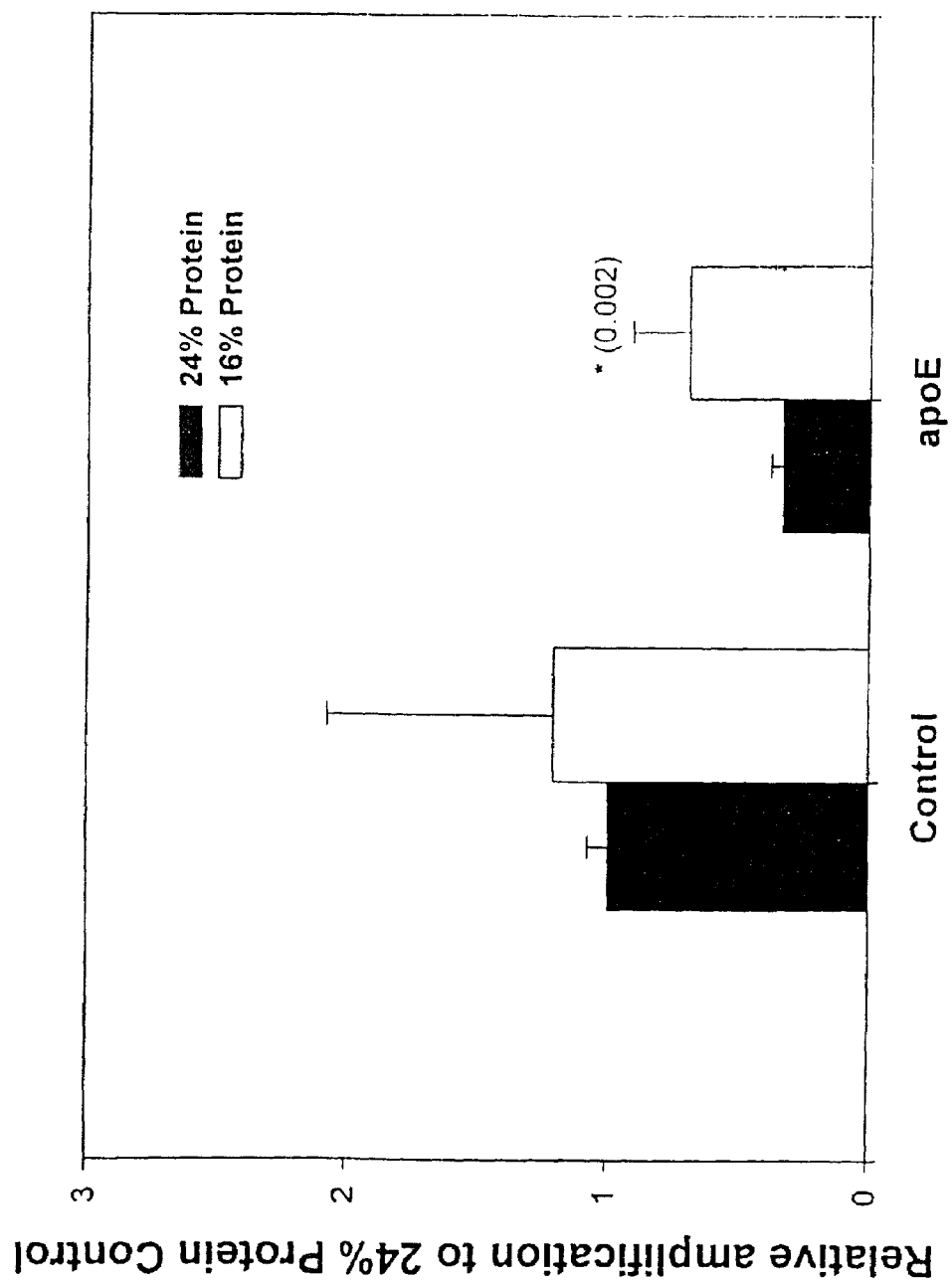

Lipid peroxidation levels were measured by determining the levels of MDA and 4-HNE. The hyperclolesteremic apoE mice had significantly increased levels of lipid peroxides compared to control mice (P<0.05). However, in contrast with the results observed with the total cholesterol levels, the degree of lipid peroxidation did not significantly increase in apoE mice on the western compared to the chow diet (FIG. 8). By contrast, the control mice fed the western diet sustained increased lipid peroxidation compared to the chow diet (P<0.05). Hence, while the apoE mice always had the highest levels of lipid peroxides compared to the control mice, the degree of lipid peroxidation in apoE did not increase when fed the western diet compared to the chow diet.

EXAMPLE 14

Histology in Mice

One aorta from each group was embedded in paraffin, and cut into 5 micron cross-sections that were stained with hematoxylin and eosin. While atherosclerotic lesions were absent in all of the 10 week age groups (control and apoE), regardless of diet (chow vs. western), atherosclerotic lesions were present in both of the 34 week old apoE group but absent in the 34 week old control mice. Qualitatively, both lesion frequency and size appeared increased in the apoE mice on the western diet relative to the chow fed apoE mice.

EXAMPLE 15

Analysis of mtDNA Damage in Human Atherosclerotic and Healthy Aortas

To determine whether increased mtDNA damage is present in human atherosclerotic tissues, DNA damage analysis was performed on age-matched atherosclerotic and healthy aortas from humans. Aortas from each group were fixed in 4% paraformaldehyde, embedded in paraffin, cut into 5 micron sections, dewaxed, rehydrated, stained with hematoxylin and eosin, and atherosclerotic lesion development assessed.

Figure 9:
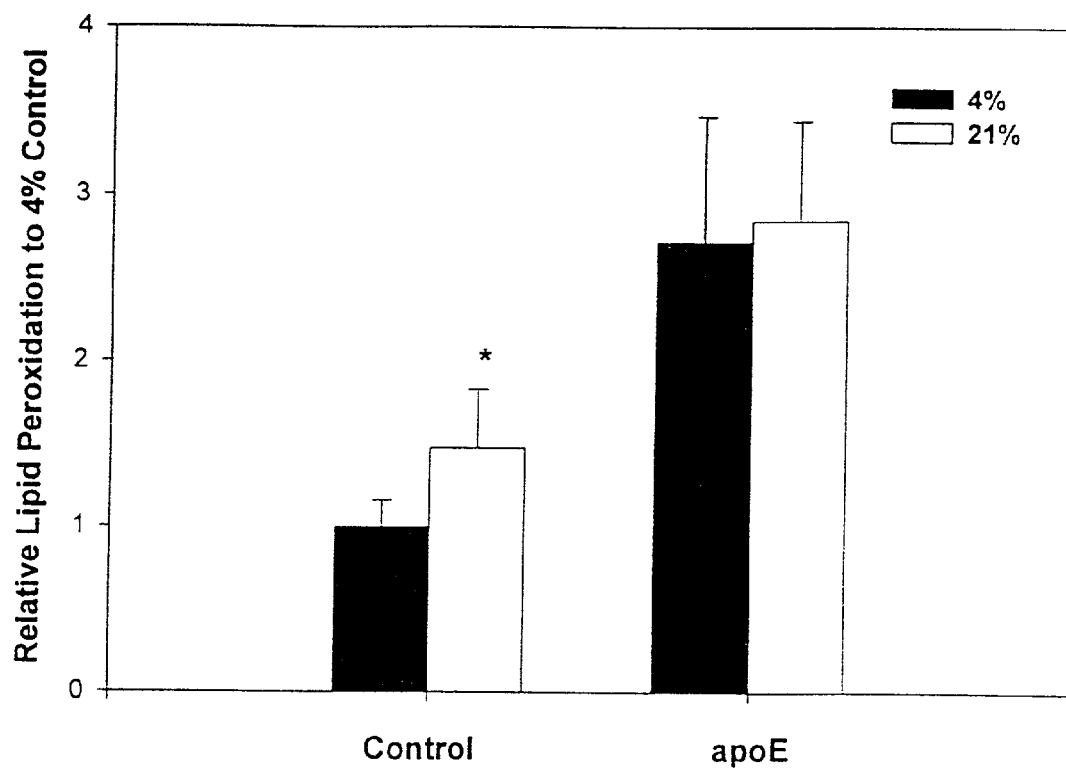
FIG. 9 shows QPCR of age-matched normal and atherosclerotic aortic mtDNA from humans. The 16.2 kb (upper row) and 0.22 kb (bottom row) products represent the long and short human QPCR amplicons, respectively. Methods for QPCR from human mtDNA have been previously described (Ballinger, 1996, 1999; Yakes, 1997).

QPCR analysis revealed significantly increased mtDNA damage in atherosclerotic tissues compared with healthy control group aortas (FIG. 9 and Table 8). By contrast, a marker for nuclear DNA damage, the β-globin gene cluster, did not sustain significant damage in atherosclerotic aorta compared with controls (P=0.15). Consequently, the mtDNA sustained significant and preferential damage in human atherosclerotic aortas. These findings were consistent with the notion that mtDNA damage is an integral feature of atherogenesis. Because increased mtDNA damage was a consistent feature in both human and mouse atherogenesis, it was hypothesized that mitochondrial dysfunction is an important event in atherogenesis, possible modulating the phenotype of vascular cells that are integral to atherosclerotic lesion formation.

TABLE 7 mtDNA Lesions/10 kb in Healthy and Atherosclerotic Human Aortas

| Normal | Atherosclerotic | P Value |
|---|---|---|
| 0.0 (0.06) | 0.67 (0.23) | 0.04 |

Table 7 shows estimated mtDNA lesions per 10 kb from human healthy and atherosclerotic aorta. The mean lesion frequency (± SEM) for the atherosclerotic aortas is expressed relative to the normal group (designated as the "zero" class, 0.0 ± 0.06 lesions/10 kb). Statistical analysis (independent Student's t test) revealed significant differences between normal and atherosclerotic aortas.

EXAMPLE 16

Analysis of Artherogenesis and mtDNA damage in apoE (−/−), SOD2 (+/−) Mice

To test the hypothesis that mitochondrial dysfunction is an important event in atherogenesis, an experiment was undertaken to determine whether perturbation of mitochondrial antioxidant capacity would accentuate mtDNA damage and atherogenesis. SOD2 was chosen as a target for perturbation because of its importance in maintaining the mitochondrial redox state. Although SOD2 (−/−) knockout mice die within two week of birth, rendering their use for these studies impractical, previous studies of heterozygous (+/−) SOD2 mice in the C57BL/J6 background have demonstrated decreased mitochondrial function and SOD2 activity compared to wild type mice (62, 65). In addition, examining SOD2-mediated effects on mitochondrial function in atherogenesis was of particular interest, given the regulation of SOD2 by shear stress forces and the putative role of shear stress forces in atherogenesis (66). Thus, to determine whether compromised mitochondrial function and antioxidant activity (MnSOD, SOD2) affects atherogenesis, an apoE (−/−), SOD2 (+/−) mouse was developed.

Figure 10:
FIGS. 10A and 10B show that hybrid apoE (−/−), SOD2 (+/−) mice have increased atherosclerotic lesions and mtDNA damage.

For analysis of atherogenesis and mtDNA damage, apoE (−/−), SOD2 (+/−) mice and apoE (−/−) controls were fed a 4% fat diet and sacrificed at 17 weeks of age. Assessment of functional SOD2 acitivity in hybrid apoE (−/−), SOD2 (+/−) aortas demonstrated a 44% reduction of activity compared with "normal" apoE (−/−) mice (data not shown; P<0.001). Histological examination of atherosclerotic lesion development in these mice revealed that apoE (−/−), SOD2 (+/−) mice developed earlier lesions at physiologically relevant sites, including in the ascending aorta at the origin of the cerebral vessels. However, the most impressive finding was that at 17 weeks of age, oil-red-O positive lesions were present throughout the descending aorta at virtually every branch point of the spinal arteries in the apoE (−/−), SOD2 (+/−) mice (FIG. 10A). Analogous lesions were rare in both 17-week-old and 34-week-old apoE (−/−) mice. Overall, the apoE (−/−), SOD2 (+/−) mice had 2.5 fold as many atherosclerotic lesions (P=0.02) compared with apoE (−/−) littermates (FIG. 10B). Although the small size of atherosclerotic, lesions at the branch points precluded direct measurement of mtDNA damage at these sites, quantification of aortic mtDNA damage through QPCR revealed increased aortic mtDNA damage in the apoE (−/−), SOD2 (+/−) mice compared with their age-matched apoE (−/−). littermates (Table 8; P=0.006). Thus, while providing further evidence that mitochondrial dysfunction resulting from oxidative mtDNA damage is important in atherogenesis, these findings also supports the notion that, under normal circumstances, decreased expression of SOD2 in response to turbulent flow at arterial branch points promotes atherogenesis at these sites.

TABLE 8

Lesion Frequencies/10 kb in 3-Week-Old Control and apoE (−/−) Aortas

| Control | apoE (−/−)/SOD2 (+/−) | P value |
|---|---|---|
| 0.0 (0.097) | 0.68 (0.17) | 0.006 |

Table 8 shows relative aortic mtDNA damage between apoE (−/−), SOD2 (+/−) and apoE (−/−) littermates (n = 12). apoE (−/−) littermates served as the controls in this series of experiments, and thus, are designated as "zero-class" ($A_0$) lesion frequencies. Lesion frequencies are expressed as mean and (SEM).

EXAMPLE 17

Discussion of In Vitro Experiments

The present study was designed to demonstrate that hydrogen peroxide and peroxynitrite mediate mitochondrial damage and dysfunction in HUVEC and HASMC in vitro. Mitochondrial DNA damage was significant in both cell types treated with hydrogen peroxide, and HUVEC had significant nDNA damage. Similarly, the mitochondrial DNA was significantly damaged when exposed to acute doses of peroxynitrite in HUVEC (0.1 mM and 0.5 mM) and HASMC (0.5 mM). Moreover, when treated with low, sustained levels of peroxynitrite, significant mitochondrial DNA damage relative to controls was observed in HUVEC, while the nDNA remained unaffected. Similarly, SIN-1 treatments also resulted in significantly increased mitochondrial DNA damage in HUVEC. By contrast, SIN-1 treatment of HASMC did not cause significant levels of damage, which would appear inconsistent with the effects of peroxynitrite treatment (Table 1). These differences may be due to the relative ability of HASMC to reduce $O_2^-$ and hydrogen peroxide compared to HUVEC. This would be consistent with the results of the XO/LZ treatments in HASMC that did not cause significant levels of damage, whereas the same exposure in HUVEC caused significant mitochondrial DNA damage (Table 1). These results, plus the fact that HUVEC, in general, appear more sensitive to reactive oxygen species treatments, would be consistent with this notion.

The level of ND2 and Cyt b transcripts declined subsequent to peroxynitrite treatment in both cell types. Although both ND2 and Cyt b levels were substantially decreased, only the Cyt b transcript levels were significantly reduced (HASMC, P=0.033; HUVEC, P=0.011). ND2 and Cyt b transcript reduction appeared transient, with most cultures recovering to the levels of untreated controls after removal of reactive oxygen species treated media and 2 hours in conditioned media. Consequently, transcript reduction was directly associated with the acute reactive oxygen species exposure. Because the Cyt b transcript is the most distant from the transcription initiation site for the polycistronic mtRNA transcript (43-46), those genes furthest from the initiation site may be more (transcriptionally) affected by random mitochondrial DNA damage. Alternatively, transcript stability in the presence of specific reactive oxygen species may play a role in RNA levels. Results from actinomycin D experiments suggest that both transcriptional inhibition and transcript instability occur in response to peroxynitrite treatment when examining Cyt b, while the ND2 transcript appears less prone to peroxynitrite induced instability. Finally, mitochondrial rRNAs are subject to preferential expression (47, 48), potentially making them less prone to the effects of peroxynitrite treatment used in this study.

Consistent with the decreased transcript levels, a concomitant decline in mitochondrial protein synthesis was observed in both HUVEC and HASMC treated with acute doses of reactive oxygen species. Protein synthesis was decreased by 23%-33% in both cell lines treated with 0.2 mM $H_2O_2$, while 0.5 mM peroxynitrite treatment resulted in more substantial losses in protein labeling (HASMC, 30% of control; HUVEC, 45% of control). Also consistent with these findings were the reductions in cellular ATP production and respiration that occurred subsequent to reactive oxygen species treatments. Consequently, these in vitro results suggest that reactive oxygen species can mediate a series of related events associated with mitochondrial function in HUVEC and HASMC that ultimately result in cellular dysfunction.

While the mitochondria are the major producers of cellular ATP, they are also chronic generators of reactive oxygen species (12-16), creating $O_2^-$ during electron transport (metabolic processes). $O_2^-$ is subsequently removed by the mitochondrial manganese superoxide dismutase (Mn-SOD, SOD2), but this reaction produces hydrogen peroxide which accumulates in the mitochondria. Alternatively, $O_2^-$ reacts with nitric oxide at near diffusion rates ($6.7 \times 10^9$ $M^{-1}$ $sec^{-1}$) to form peroxynitrite (49).

While nitric oxide is known primarily for having an anti-atherogenic role (50-52), these effects are diminished in atherosclerotic vessels due to reaction of nitric oxide with $O_2^-$ to form peroxynitrite. Peroxynitrite readily oxidizes LDL and depletes several antioxidants (10, 11). Therefore, peroxynitrite produced in the artery wall may directly promote ox-LDL formation, which in turn, can lead to mitochondrial dysfunction (53). For example, treatment of fibroblasts with ox-LDL leads to mitochondrial dysfunction (53). Similarly, clinically relevant levels of ox-LDL increase hydrogen peroxide production 4-12 fold in endothelial cells (54). In vivo studies have confirmed that oxidants derived from nitric oxide (e.g. peroxynitrite) are generated in human coronary arteries, and moreover, are concentrated in and around foam cells within the atheroma deposits as well as in early subintimal fatty streaks (55, 56). In addition, peroxynitrite mediates nitration of MnSOD (mitochondrial form of SOD) at tyrosine residues, resulting in its inactivation (57, 58). Peroxynitrite treatment of recombinant human MnSOD resulted in complete inhibition of enzymatic activity and formation of both nitrotyrosine and dityrosine (57, 58). Hence, because atherosclerotic vessels are deficient in endothelial nitric oxide production (59), and since the relative ratio of nitric oxide t o $O_2^-$ appears important in the role of nitric oxide as an anti- or pro-oxidant (5, 60), the bioactivity of nitric oxide in these cells may serve as more of a pro-oxidant than an antioxidant, setting up a cycle of continued endothelial cell damage. Additional studies comparing the level of mitochondrial DNA and nDNA damage from a limited number of age-matched atherosclerotic vs. healthy aortas, which show that diseased aortas have significantly increased levels of mitochondrial DNA damage (P=0.0023), are consistent with these reports. Consequently, peroxynitrite appears to mediate a variety of deleterious effects upon the cell, including mitochondrial DNA damage, altered transcript and protein levels, and reduction in mitochondrial antioxidant activity.

The role of nitric oxide has also been examined in elimination of oxidants derived from the mitochondria in human placental trophoblast cells (HPTC) (61). When nitric oxide production is reduced in human placental trophoblast cells by using L-NAME, an inhibitor of nitric oxide synthetase, cell oxidant formation increases as expected. Treatment of human placental trophoblast cells with CuZnSOD and catalase does not attenuate the evoked oxidant response due to NOS inhibition. Use of additional inhibitors of xanthine oxidase, cyclooxygenases, and mitochondrial OXPHOS demonstrate that only the mitochondrial OXPHOS inhibitors enhance the oxidant response induced by nitric oxide synthetase inhibition, while inhibitors of XO and cyclooxygenases do not. This implies that reactive oxygen species generated by the mitochondria serve as major damaging agents in the cell, and that regulation of nitric oxide synthetase may play an important role with regard to mitochondrial generated reactive oxygen species.

In the oxidative environment of the artery, vascular endothelial and smooth muscle cells are chronically stressed by reactive oxygen species. Consequently, cells that can no longer respond properly to oxidative stress are at greater risk for the deleterious effects of reactive oxygen species mediated damage. It has been shown herein that HAMSC and HUVEC (especially HUVEC) are sensitive to such damage in vitro, and therefore, that the chronic, in vivo production of reactive oxygen species most likely mediates vascular cell dysfunction by initiating mitochondrial decline, resulting in loss of many important cellular functions.

EXAMPLE 18

Discussion of Experiments with Mice

The primary objective of this study was to examine the degree of DNA damage in aortic and heart tissues from age-matched hypercholesteremic apoE and control mice. The apoE mouse develops atherosclerotic lesions in a fashion similar to humans. Atherogenesis is generally hastened when apoE mice are fed a high fat western diet compared to a chow diet. For example, monocyte attachment to endothelial cells occurs as early as 6 (western) or 8 (chow) weeks of age, followed by foam cell development as early as 8 (western) or 10 (chow) weeks of age, with advanced lesions evolving as early as 15 (western) or 20 (chow) weeks of age. The degree and progression of atherogenesis in the apoE mice used in this series of experiments was consistent with previous observations.

Mitochondrial DNA damage was significantly increased in aortas from both the 10 and 34 week-old hypercholestermic apoE mice fed the chow diet compared to their age-matched c57B1controls. Age was also associated with a direct increase in estimated mitochondrial DNA lesion frequency in the apoE mice ($P<0.05$), regardless of diet. Because additional analyses comparing the relative levels of mitochondrial DNA damage between proximal and distal ends of the aorta in apoE showed no significant differences in mitochondrial DNA damage within each group, it is unlikely that the mitochondrial DNA damage observed in apoE aortas is an artifact of atherogenic factors specific to the proximal aorta. By contrast, increased mitochondrial DNA damage occurred throughout the apoE aorta, and thus, is not a product of atherosclerotic lesion development, but is potentially a factor contributing t o atherogenesis.

The western fed apoE mice did not have significantly increased mitochondrial DNA damage compared to their chow fed apoE counterparts. In this regard, total cholesterol and lipid peroxidation levels in each group of mice were assessed. While the western diet was also associated with significantly higher cholesterol levels compared to the chow diet in the apoE mice ($P<0.05$), it did not result in a significant increase in lipid peroxidation in the apoE mouse compared to the chow diet. Consequently, these data suggest that lipid peroxidation levels are already maximized in the chow fed apoE mice (potentially due to their genotypic predisposition for hypercholesteremia). Accordingly, the higher fat western diet failed to induce increased lipid peroxidation in the apoE mice relative to the chow diet, which is consistent with the mitochondrial DNA damage results showing no differences between the chow and western diets in apoE mice. Consequently, while the western diet can cause an increase in total cholesterol relative to the chow diet, the western diet does not significantly increase the overall levels of peroxidized lipids in apoE mice, and thus, may reflect why the mitochondrial DNA damage correlates more closely with genotype and age, but not diet, in apoE mice. As expected, the hypercholesteremic apoE mice had significantly elevated cholesterol (4.2-5.7 fold higher, $P<0.001$) and lipid peroxidation (1.9-2.7 fold higher, $P<0.05$) levels relative to the "healthy" age-matched controls. While it has been shown that an age related increase in lipid peroxidation in apoE mice exists compared to age-matched control mice, no reports could be found comparing lipid peroxidation levels between chow and western diets. Consequently, the results herein indicate that while the western diet results in significantly elevated cholesterol levels compared to the chow diet in apoE, it does not change the overall level of lipid peroxidation products.

While age and high fat diet were not associated with significantly increased mitochondrial DNA damage in the c57B1mice, a substantial increase of mitochondrial DNA damage was seen in chow fed controls with age, and a trend of increased damage with the western diet was observed in the 10 week old mice. Increased age appeared to affect the chow fed control mice while less difference was seen in the western diet fed mice. The 10 week old western diet-fed control mice also had higher estimated mitochondrial DNA lesion frequency compared to chow-fed, whereas no association of diet and mitochondrial DNA damage could be seen in the 34 week-old control mice, suggesting that the effects of diet on mitochondrial DNA damage have the greatest effect in the young control mice. In contrast with the results observed in the apoE mice, the western diet was associated with a significant ($P<0.05$) increase in lipid peroxidation relative to the chow diet in the control mice, implying that lipid peroxidation is not at maximal levels in "healthy" mice fed the chow diet, and by elevating the substrate levels (i.e. western diet), lipid peroxidation products increased in control mice, which would be consistent with the increased mitochondrial DNA damage observed in the control mice fed the western diet.

Caloric restriction and decreased dietary protein content have been reputed to have beneficial effects upon a variety of organisms, increasing life span. Consequently, the fact that both lines of mice sustained significantly less mitochondrial DNA damage on diets containing less protein compared to higher protein would be consistent with this notion. Longitudinal studies of apoE mice on calorically restricted diets are needed to more fully address this finding. Because low calorie diets are associated with decreased reactive oxygen species levels, these findings are consistent with the notion that decreased reactive oxygen species-mediated damage inhibits atherogenesis.

Evidence for a mitochondrial role (damage and dysfunction) in a variety of chronic, age related diseases has accumulated over the past decade. A basic paradigm is that mitochondrial damage accumulates over time in tissues, causing cellular OXPHOS potentials (energy capacities) to decline while OXPHOS-mediated reactive oxygen species production increases, manifesting in cellular dysfunction. While it has been shown that endothelial cell mitochondria are susceptible to reactive oxygen species mediated damage in vitro, reports of increased pathogenic mitochondrial DNA mutations in cardiovascular tissues from atherosclerotic humans exist, as do pathogenic mitochondrial DNA mutations associated with the risk factors for heart disease (age, smoking, diabetes, etc.). Interestingly, risk factors such as smoking, hypertension, hypercholesteremia, etc. mediate increased reactive oxygen species production, and past reports have shown that the mitochondria appear a susceptible target for damage. While atherogenesis is certainly a complex process involving a variety of required steps, it is proposed herein that a basic mechanism for atherosclerotic lesion development begins with accumulation of vascular tissue mitochondrial damage, ultimately leading to OXPHOS dysfunction, and compromised energetic capacities. The synergism of these processes result in increased reactive oxygen species production (a feature already noted in atherosclerotic tissues) and vascular cell dysfunction, creating an atherogenic environment within the artery.

This is the first report investigating the level of mitochondrial DNA damage in aortic tissues from a mouse model of atherosclerosis compared to age-matched controls. These results show a clear increase in mitochondrial DNA damage associated with atherogenesis and age. Due to the presence of significant mitochondrial DNA damage in the 10 week-old apoE mice, it would appear that damage occurs prior to, or simultaneous with, atherosclerotic lesion development in this model of atherosclerosis in vivo. In addition, aortic mitochondrial DNA damage increases with age in vivo. Moreover, the apoE genotype appears to have a greater influence on the level of mitochondrial DNA damage compared to diet, although dietary effects on mitochondrial DNA damage may exist in the young "healthy" c57B1mice. Consequently, mitochondrial DNA damage observed in the apoE mice may ultimately result in compromised OXPHOS processes and thereby initiate endothelial cell dysfunction, the key event in atherogenesis.

EXAMPLE 19

In Vivo Measurements of Mitochondrial DNA Damage

Figure 11A:
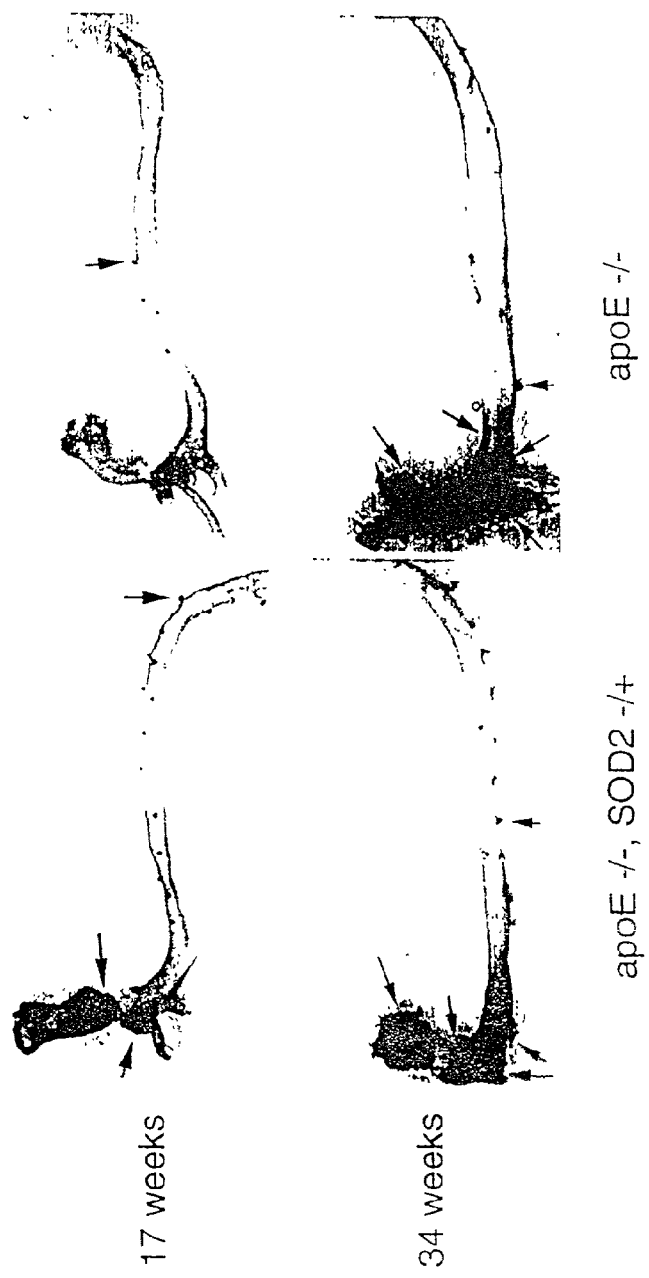
FIG. 11 shows the increased incidence of mitochondrial DNA damage in patients with risk factors for myocardial infarction. Blood samples were taken at the time of cardiac catherization to measure mitochondrial DNA damage by QPCR. For this figure, values of mitochondrial DNA damage above the mean for. a "normal" population were considered increased. The bar graphs show the percentage of patients in each category with increased mitochondrial DNA damage. The occurrence of increased mitochondrial DNA damage is more frequent in subjects with hypertension, cigarette smoking, diabetes and combinations of these risk factors for inyocardial infarction.
Figure 11B:
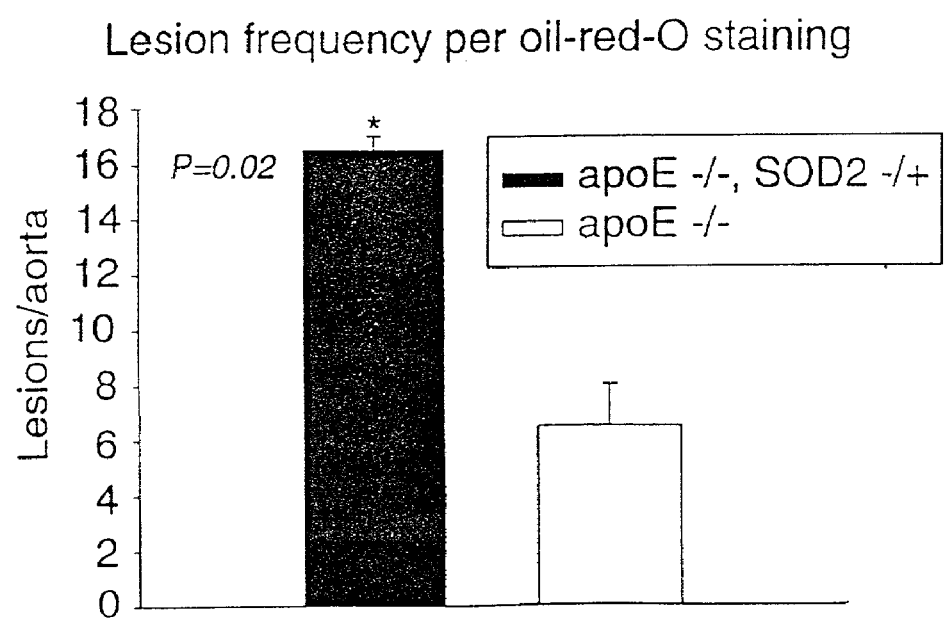

Patient who were undergoing cardiac catherization were recruited for an in vivo study of mitochondrial DNA damage. All signed informed consent for an additional blood sample to be taken at the time of cardiac catherization. In all, there were 75 patient. White blood cells were isolated by standard techniques (the "buffy coat" preparation), and DNA (both nuclear and mitochondrial) was isolated. Mitochondrial DNA damage was determined by quantitative PGR using both "short mitochondrial DNA fragments" and damage within the β-globin gene as controls. FIG. 11 shows the increased incidence of mitochondrial DNA damage in patients grouped according to risk factors associated with myocardial infarction.

Based upon initial results, a certain level of mitochondrial DNA damage was designated normal. Above this level, the damage was considered high. The percentage of patients who had mitochondrial DNA damage as a function of cardiac risk factors was then determined. For example, in those who smoked, approximately 50% had increased mitochondrial DNA damage, while in those who did not smoke, less than 20% had increased mitochondrial DNA damage. In some cases, the effects were additive, in that 100% of patients who smoked and were diabetic had increased mitochondrial DNA damage. In this analysis, having a risk factor was significantly different than not having a risk factor (e.g. smoking (p<0.05); smoking plus diabetes (p<0.01); smoking plus hypertension (p<0.05)). It was also determined that there was a trend towards the presence of coronary artery disease based upon the extent of mitochondrial DNA damage. However, a larger study group of patients is required to determine the degree of significance to this trend.

Figure 12:
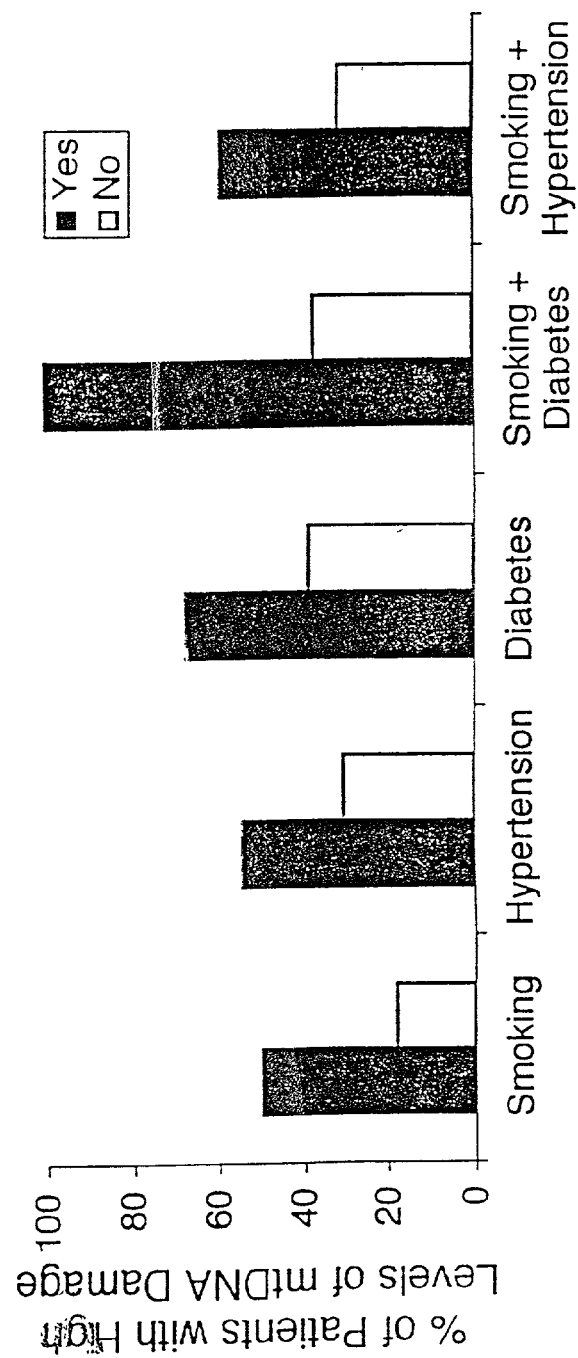
FIG. 12 shows mitochondrial DNA damage before and after a 20 mile "training run". Blood samples were taken, a buffy coat was obtained and mitochondrial DNA damage was assessed by QPCR Although mitochondrial DNA damage is present immediately after the training run, this quickly returns to normal values as shown here.
Figure 13:
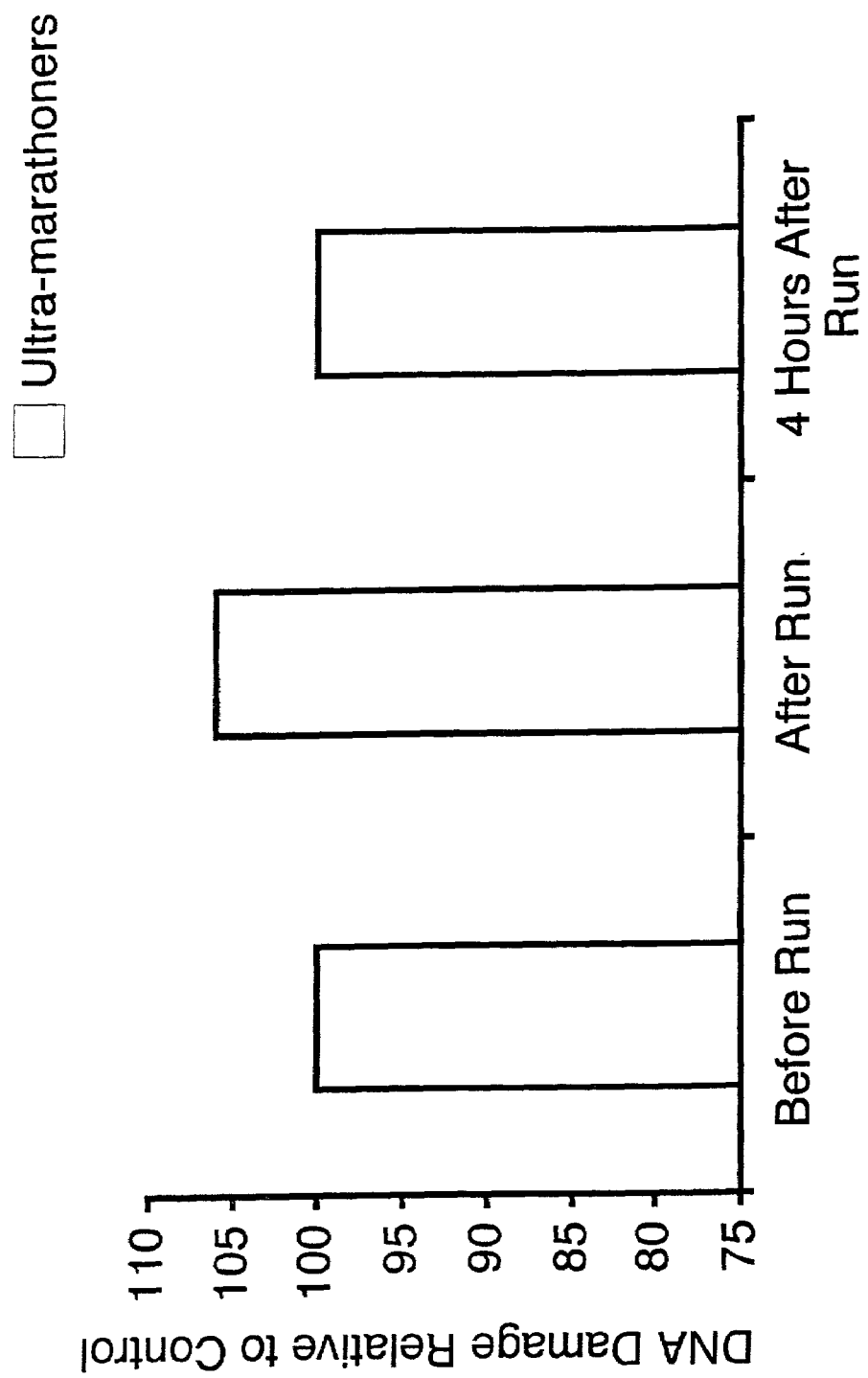
FIG. 13 shows that ultra marathoners had significantly less mitochondrial DNA damage after being fed a high fat meal than did the control subjects. In all cases, mitochondrial DNA damage was assessed before, immediately after eating a high fat meal and 4-6 hours later. The observed mitochondrial DNA damage in controls reflects the immediate effects of dietary intake of ROS in the form of fats and cholesterol. The relative "protection" observed in the ultra marathoners may relate to an upregulation of anti-oxidant defense mechanisms in these individuals.
Figure 14:
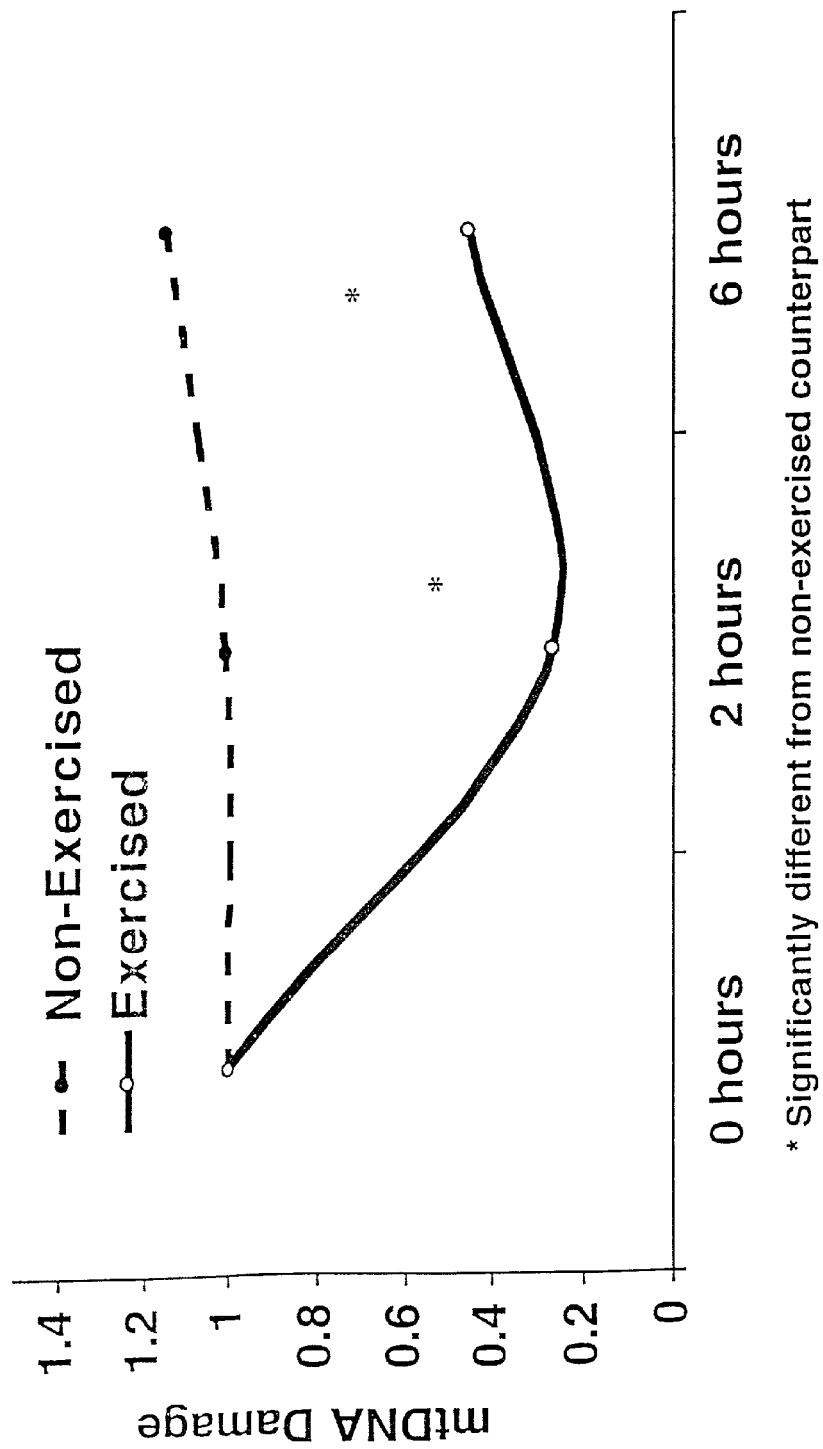
FIG. 14 shows that ultra marathoners had significantly less protein damage after being fed a high fat meal than did the control subjects.
Figure 15:
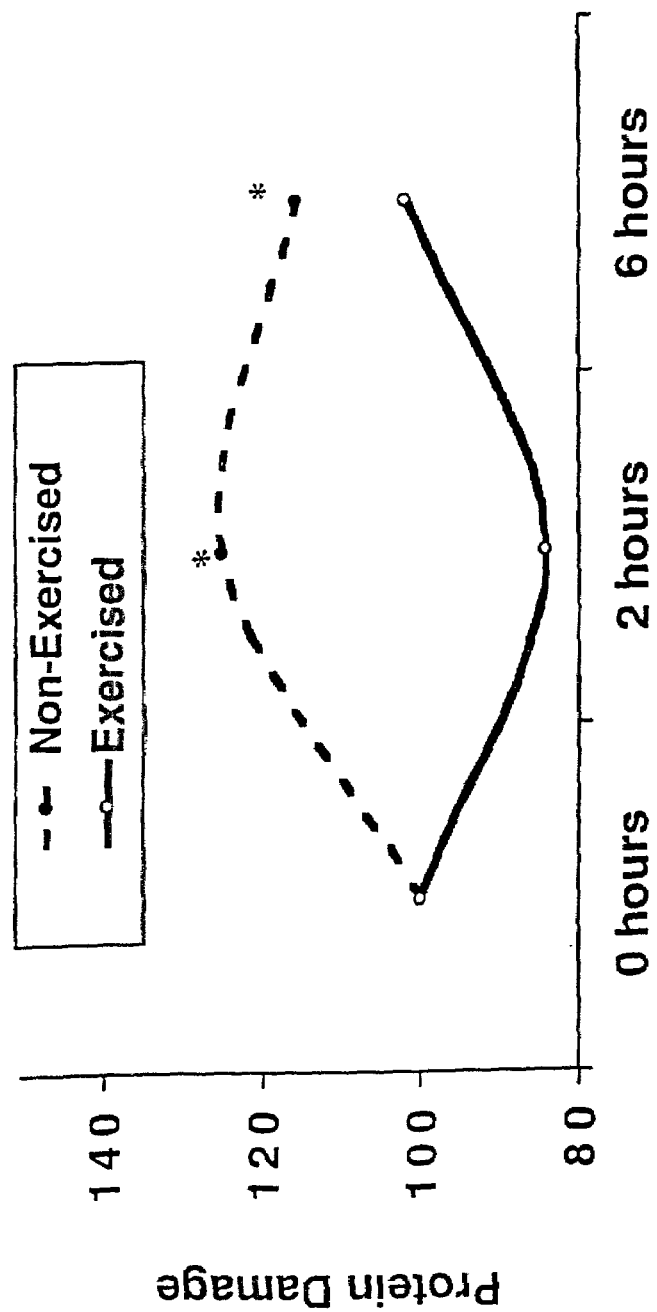

To examine further the extent of mitochondrial DNA damage under a variety of in vivo conditions, 5 individuals who are "ultra marathoners" and an age-matched group of 6 individuals who are healthy and active, but not ultra marathoners, were examined. First, mitochondrial DNA damage was measured before and after a 20 mile "training run" by the ultra marathoners. Blood samples were taken, a buffy coat was obtained, and mitochondrial DNA damage was assessed. FIG. 12 shows that there is a mild increase in mitochondrial DNA damage just after the run, which returns to normal within 4 hours. On a different day, the ultra marathoners and the control subjects were fed a high fat meal. The high fat meal comprised the "El Grande Platter" at a local Mexican food restaurant, which contained approximately 3000 calories, of which approximately 60-70% were fat calories. Blood samples were taken just before the meal, and 2 and 6 hours after. Buffy coats and DNA isolation were performed. Mitochondrial protein damage was also quantitated using white blood cell mitochondrial protein as a source. FIGS. 13 and 14 show that there is a gradual, small increase in mitochondrial DNA damage in the controls, and increased mitochondrial protein damage at 2 hours that decreasess in 4 hours. In the ultra marathoners, mitochondrial DNA damage and protein damage actually decreased to below baseline levels at 2 hours and begins returning to baseline by 6 hours. Presumably, since the ultra marathoners are subjected to increased oxidative stress when they run, their anti-oxidant protective systems are more effective. Thus, when exposed to a stimulus for DNA damage, the ultra marathoners have even less damage than normal. Subsequently, their antioxidant systems are activated and decrease their oxidant levels to below resting levels.

EXAMPLE 20

Effects of mtDNA Damage on Artherogenesis

Comparison of the level of mtDNA damage atherosclerotic aortic tissues with age-matched controls shows that increased mtDNA damage is clearly associated with atherogenesis. Due to the presence of significant mtDNA damage in the 3 and 10 week-old apoE (–/–) mice, it appears that damage occurs prior to, or simultaneously with, atherosclerotic lesion development in vivo. Furthermore, because both atherosclerotic lesion frequency and aortic mtDNA damage are increased in hybrid apoE (–/–), SOD2 (+/–) compared with apoE (–/–) littermates, it is clear that mitochondrial function is important in atherogenesis.

The data reported here provides the first mechanistic evidence or a role for mitochondrial dysfunction in atherogenesis, indicating that: 1) mtDNA damage is significantly increased in both human and mouse atherosclerotic aorta; 2) Aortic mtDNA damage increases with age in vivo; 3) mtDNA damage occurs prior to or coincident with atherosclerotic lesion development in vivo; 4) measurement of mtDNA at an early stage provides an accurate assessment of reactive species and oxidative damage-mediated atherosclerotic risk; and, 5) the putative role of SOD2 in preventing atherogenesis in areas of turbulent flow may involve protection o f the mitochondrial genome from oxidative damage. Because oxidative stress is present in individuals with many of the traditional risk factors for atherosclerosis (cigarette smoking, diabetes mellitus, hypotension, hypercholesteremia, hyperhomocysteinemia, and increased age) suggests that mtDNA damage and the resulting mitochondrial dysfunction represent common mechanisms by which these factors contribute to atherogenesis.

When considering the notion that mtDNA damage and mitochondrial reactive species generation are important mediators of vascular cell function and atherogenesis, it is useful to recall that atherogenesis occurs preferentially at sites of disturbed flow and decreased shear stress (67). In Vitro and in vivo alterations in shear stress result in altered gene expression (66). Interestingly, manganese superoxide dismutase (SOD2; the predominant mitochondrial antioxidant enzyme) is among the genes that are regulated by sheer stress forces (66). Because SOD2 expression is increased under conditions of high shear stress forces and decreased at branch points in vivo, susceptibility of mitochondria to reactive species mediated damage would be greatest at these sites, consistent with the observation herein.

In summary, atherogenesis is a complex process involving many interrelated steps. It has become increasingly clear that inflammatory responses involving cytokines, chemokines, growth factors and other vasoactive molecules are an important component of this process. The hypothesis that mtDNA damage is am important initiating event in atherogenesis is complementary to "inflammatory response: theories. Increased reactive species production from exposure of the vascular endothelium to an inflammatory milieu results in endothelial dysfunction, inflammatory cell attachment and initiation of atherosclerotic lesion formation. The mtDNA damage reported here contributes to compromised metabolic processes (in particular, oxidative phosphorylation) that likely participate in both endothelial cell dysfunction and vascular smooth muscle cell phenotypic alterations, which are key components of atherogenesis. Thus, the findings herein are consistent with the theory that accumulation of reactive oxygen and other reactive species-mediated mitochondrial damage in vascular tissues leads to compromised vascular cell energetic capacities and dysfunction, important early events in atherogenesis.

The following references were cited herein:
1. Carpenter et al. (1995) *Athersclerosis* 118, 169-172.
2. Halliwell, B. (1989) *British J Exper Path* 70, 737-757.
3. Berliner et al. (1996) *Free Rad Biol Med* 20, 707-727.
4. Massaeli et al. (1995) *Cardiovascular Res* 29, 597-603.
5. Freeman et al. (1995) *Adv Pharmacol* 34, 45-69.
6. Corral-Debrinski et al. (1992) *Mut Res* 275, 169-180.
7. Parthasarathy et al. (1992) *Prog Lipid Res* 31, 127-143.
8. Berliner et al. (1995) *Circulation* 91, 2499-2496.
9. Kimura et al. (1995) *Atherosclerosis* 118, 1-8.
10. Darley-Usmar et al. (1992) *Free Radical Res Commun* 17, 9-20.
11. Graham et al. (1993) *FEBS Lett* 330, 181-185.
12. Forman, et al. (1982) In Free Radicals in Biology, Vol V, ed. Prior, W. A. (Academic Press, Orlando), pp. 65-90.
13. Turrens, et al. (1980) *Biochem J* 191, 421-427.
14. Boveris, et al. (1980) In Chemical and Biochemical Aspects of Superoxide and Superoxide Dismutase, Vol I, eds. Bannister, et al. (Elsevier, Amsterdam), pp. 84-91.
15. Chance et al. (1979) *Physiol Rev* 59, 527-604.
16. Breen et al. (1995) *Free Rad Biol Med* 18, 1033-1077.
17. Chen et al. (1994) *Proc Natl Acad Sci USA* 91, 4130-4134.
18. Zhang et al. (1990) *J Biol Chem* 265, 16330-16336.
19. Bandy et al. (1990) *Free Rad Biol Med* 8, 523-539.
20. Ferrari et al. (1985) *J Mol Cell Cardiol* 17, 937-45.
21. McCord, J. M. (1988) *Free Rad Biol Med* 4, 9-14.
22. Giulivi et al. (1995) *Arch Biochem Biophys* 316, 909-916.
23. Bindoli A. (1988) *Free Rad Biol Med* 5, 247-261.
24. Hruszkewyca, A. M. (1992) *Mut Res* 275, 243-248.
25. Yakes et al. (1997) *Proc Natl Acad Sci* 94, 514-519.
26. Adachi et al. (1993) *Biochem Biophys Res Commun* 195, 945-951.
27. Trounce et al. (1989) *Lancet* 1, 637-639.
28. Cortopassi et al. (1990) *Nucleic Acids Res* 18, 6927-6933.
29. Sastre et al. (1996) *Hepatology* 24, 1199-1205.
30. Iyer et al. (1961) *Nature* 192, 535-541.
31. Beckman et al. (1990) *Proc. Natl. Acad. Sci. USA* 87, 1620-1624.
32. Ballinger et al. (1996) *Cancer Res* 56, 5692-5697.
33. Yakes et al. (1996) In Technologies for detection of DNA damage and mutations, ed. Pfeifer, G. P. (Plenum, NY), pp. 169-182.
34. Chirgwin et al. (1979) *Biochemistry* 18, 5294-5299.
35. Torroni et al. (1990) *J. Biol. Chem.* 265, 20589-20593.
36. Bogenhagen et al. (1978) *J. Mol. Biol.* 119, 69-81.
37. Ballinger et al. (1992) *Nature Genet* 1, 11-15.
38. Slater et al. (1963) *Biochim Biophys Acta* 77, 383-393.
39. Berg et al. (1990) *APMIS* 98, 152-162.
40. Lippold H J. (1982) *Histochemistry* 76, 381-405.
41. Schanenstein E, Hoffer-Bergthaler E. (1972) *Monatshefte fur Chemie* 103, 1271-1275.
42. Huet et al. (1992) *Cytometry* 13, 532-539.
43. Ojala et al. (1980) *Cell* 22, 393-403.
44. Ojala et al. (1981) *Nature* 290, 470-474.
45. Attardi et al. (1985) In Achievements and Perspectives of Mitochondrial Research, eds. Qkuagliarello, et al., (Elsevier Science, NY), pp. 145-163.
46. Doerson et al. (1985) *J. Biol. Chem.* 260, 5942-5949.
47. Christianson et al. (1986) *Proc Natl Acad Sci USA* 83, 6277-6281.
48. Christianson et al. (1988) *Mol Cell Biol* 8, 4502-4509.
49. Huie et al. (1993) *Free Radical Res Commun* 18, 195-199.
50. Palmer et al. (1988) *Nature* 333, 664-666.
51. Yao et al. (1992) *Circulation* 86, 1302-1309.
52. Garg et al. (1989) *J Clin Invest* 83, 1774-1777.
53. Fossel et al. (1994) *Cancer Res* 54, 1240-1248.
54. Holland et al. (1996) *J Cell Phys* 166, 144-151.
55. Leeuwenburgh et al. (1997) *J BiolChem* 272, 1433-1436.
56. Beckmann et al. (1994) *Biol Chem* 375, 81-88.
57. MacMillan-Crow et al. (1996) *Proc Natl Acad Sci USA* 93, 11853-11858.
58. MacMillan-Crow et al. (1998) *Biochemistry* 37, 1613-1622.
59. Lloyd-Jones et al. (1996) *Annu Rev Med* 47, 365-375.
60. Darley-Usmar et al. (1995) *FEBS Letters* 369, 131-135.
61. Goda et al. (1996) *Am J Physiol* 271, H1893-H1899.
62. Leibovitz et al., (1996) *Proc Natl Acad Sci USA* 93, 9782-9787.
63, Nakishima et al. (1994) *Arterioscler Thromb* 14, 133-140.
64. Reddick et al. (1994) *Arterioscler Thromb* 14, 141-147.
65. Williams et al. (1998) *J Biol Chem* 273, 28510-28515.
66. Topper et al. (1996) *Proc Natl Acad Sci USA* 93, 10417-10422.
67. Malek et al. (1999) *JAMA* 282, 2035-2042.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of measuring the amount of oxidative stress in a human individual, comprising the steps of:
   (a) collecting a blood sample from said individual;
   (b) assessing the amount of mitochondrial DNA damage in cells from said sample wherein such amount of damage is indicative of oxidative stress in said individual.

2. The method of claim 1, wherein increased amounts of oxidative stress are predictive of atherogenesis, hypertension, diabetes mellitis, hypercholesterolemia, degenerative diseases of aging or cancer.

3. The method of claim 1, wherein said mitochondrial DNA damage is assessed by measuring the amount of DNA damage per length of mitochondrial DNA.

4. The method of claim 3, wherein said mitochondrial DNA damage is assessed by quantitative PCR.

5. The method of claim 4, wherein said DNA is treated with FAPY glycosylase prior to said PCR amplification for detection of 8-oxo-G-lesion.

6. The method of claim 3, wherein the DNA damage comprises one or more deletions, insertions or duplications.

7. The method of claim 3, further comprising determining the amount of DNA damage in a nuclear gene in said tissue of interest; and comparing the amount of DNA damage per length of DNA between said mitochondrial DNA and said nuclear gene, wherein a greater amount of mitochondrial DNA damage per length of DNA than nuclear DNA damage per length of DNA is indicative of an increased amount of oxidative stress in said individual.

8. The method of claim 1, wherein said mitochondrial DNA damage is assessed by measuring mitochondrial mRNA production.

9. The method of claim 1, wherein said mitochondrial DNA damage is assessed by measuring mitochondrial protein production.

10. The method of claim 1, wherein said mitochondrial DNA damage is assessed by measuring changes in mitochondrial oxidative phosphorylation.

11. The method of claim 1, wherein said mitochondrial DNA damage is assessed by measuring changes in mitochondrial ATP production.

12. The method of claim 1, wherein said mitochondrial DNA damage is assessed by measuring changes in mitochondrial redox state.

13. The method of claim 1, wherein cells of the sample are further defined as white cells.

* * * * *